United States Patent
Koh

(10) Patent No.: US 11,280,758 B2
(45) Date of Patent: Mar. 22, 2022

(54) SINGLE-PARTICLE BRIDGE ASSAY FOR AMPLIFICATION-FREE ELECTRICAL DETECTION OF ULTRALOW-CONCENTRATION BIOMOLECULES AND NON-BIOLOGICAL MOLECULES

(71) Applicant: BOARD OF REGENTS, THE UNIVERSITY OF TEXAS SYSTEM, Austin, TX (US)

(72) Inventor: Seong Jin Koh, Arlington, TX (US)

(73) Assignee: Board of Regents, The University of Texas System, Austin, TX (US)

(*) Notice: Subject to any disclaimer, the term of this patent is extended or adjusted under 35 U.S.C. 154(b) by 804 days.

(21) Appl. No.: 16/069,651

(22) PCT Filed: Jan. 13, 2017

(86) PCT No.: PCT/US2017/013319
§ 371 (c)(1),
(2) Date: Jul. 12, 2018

(87) PCT Pub. No.: WO2017/123857
PCT Pub. Date: Jul. 20, 2017

(65) Prior Publication Data
US 2019/0025249 A1    Jan. 24, 2019

Related U.S. Application Data

(60) Provisional application No. 62/279,385, filed on Jan. 15, 2016.

(51) Int. Cl.
*G01N 27/414* (2006.01)
*G01N 21/64* (2006.01)
(Continued)

(52) U.S. Cl.
CPC .......... *G01N 27/4146* (2013.01); *B01J 19/00* (2013.01); *B82Y 20/00* (2013.01);
(Continued)

(58) Field of Classification Search
CPC ............... G01N 27/4146; G01N 21/64; G01N 33/5438; G01N 27/4145; G01N 2458/10;
(Continued)

(56) References Cited

U.S. PATENT DOCUMENTS 5,472,881 A    12/1995    Beebe et al.
5,837,832 A    11/1998    Chee et al.
(Continued)

OTHER PUBLICATIONS

Eftekhari, Fatemeh, et al. "Nanoholes as nanochannels: flow-through plasmonic sensing." Analytical chemistry 81.11 (2009): 4308-4311.
(Continued)

*Primary Examiner* — Dennis White
(74) *Attorney, Agent, or Firm* — Meunier Carlin & Curfman LLC

(57) ABSTRACT

The invention relates generally to devices, systems, compositions, and methods for the detection of oligonucleotides, nucleic acids, antigens, antibodies, peptides, proteins, and non-biological molecules.

21 Claims, 10 Drawing Sheets

Specification includes a Sequence Listing.

(51) Int. Cl.
| | |
|---|---|
| *B01J 19/00* | (2006.01) |
| *C12M 1/34* | (2006.01) |
| *B82Y 20/00* | (2011.01) |
| *C12Q 1/6837* | (2018.01) |
| *G01N 33/543* | (2006.01) |
| *B82Y 15/00* | (2011.01) |
| *B82Y 30/00* | (2011.01) |

(52) U.S. Cl.
CPC ............ *C12M 1/34* (2013.01); *C12Q 1/6837* (2013.01); *G01N 21/64* (2013.01); *G01N 27/4145* (2013.01); *G01N 33/5438* (2013.01); *B01J 2219/00317* (2013.01); *B01J 2219/00648* (2013.01); *B01J 2219/00653* (2013.01); *B01J 2219/00722* (2013.01); *B82Y 15/00* (2013.01); *B82Y 30/00* (2013.01); *G01N 2458/10* (2013.01)

(58) Field of Classification Search
CPC ............ B01J 19/00; B01J 2219/00653; B01J 2219/00722; B01J 2219/00317; B01J 2219/00648; C12M 1/34; B82Y 20/00; B82Y 15/00; B82Y 30/00; C12Q 1/6837
See application file for complete search history.

(56) References Cited

U.S. PATENT DOCUMENTS

| | | | |
|---|---|---|---|
| 2010/0120132 A1 | 5/2010 | Koo | |
| 2010/0227416 A1* | 9/2010 | Koh | C12Q 1/6837 436/501 |
| 2010/0256016 A1 | 10/2010 | Blair et al. | |
| 2011/0212512 A1 | 9/2011 | Wang et al. | |
| 2011/0318695 A1* | 12/2011 | Hwang | B82Y 30/00 430/322 |
| 2012/0122732 A1 | 5/2012 | Wang et al. | |
| 2012/0208290 A1 | 8/2012 | Lee et al. | |

OTHER PUBLICATIONS

U.S. Patent and Trademark Office. International Search Report and Written Opinion. Application No. PCT/US2017/013319, dated Apr. 7, 2017. 16 pages.
Adler, et al., "Sensitivity by combination: immuno-PCR and related technologies." Analyst 133, 702-718 (2008).
Ahmadi, et al., "Shape-Controlled Synthesis of Colloidal Platinum Nanoparticles", Science, 272, 1924-6 (1996).
Alhasan, et al., "Scanometric MicroRNA Array Profiling of Prostate Cancer Markers Using Spherical Nucleic Acid-Gold Nanoparticle Conjugates." Anal. Chern. 84, 4153-4160 (2012).
Ali, et al., "Rolling circle amplification: a versatile tool for chemical biology, materials science and medicine." Chem. Soc. Rev. 43, 3324-3341 (2014).
Allara and Nuzzo, "Spontaneously organized molecular assemblies. 1. Formation, dynamics, and physical properties of n-alkanoic acids adsorbed from solution on an oxidized aluminum surface", Langmuir, 1, 45-52 (1985).
Allara and Tompkins, "The study of the gas—solid interaction of acetic acid with a cuprous oxide surface using reflection—absorption spectroscopy", J. Colloid Interface Sci., 49, 410-421 (1974).
Asaga, et al., "Direct Serum Assay for MicroRNA-21 Concentrations in Early and Advanced Breast Cancer." Clinical Chemistry 57, 84-91 (2011).
Asenath-Smith, et al., "How to Prevent the Loss of Surface Functionality Derived from Aminosilanes." Langmuir 24, 12405-12409 (2008).
Bahncmann, in Photochemical Conversion and Storage of Solar Energy (eds. Pelizetti and Schiavello 1991), p. 251.

Beaucage and Carruthers, "Deoxynucleoside phosphoramidites—A new class of key intermediates for deoxypolynucleotide synthesis", Tetrahedron Lett., 22:1859-1862(1981).
Behrens, et al., "The charge of glass and silica surfaces." J. Chem. Phys. 115, 6716-6721 (2001).
Belaz, et al., "A 10-Year Retrospective Comparison of Two Target Sequences, REP-529 and B1, for Toxoplasma gondii Detection by Quantitative PCR." Journal of Clinical Microbiology 53, 1294-1300 (2015).
Benn, et al., "Comparative modeling and analysis of microfluidic and conventional DNA microarrays." Analytical Biochemistry 348, 284-293 (2006).
Braun, et al., "DNA-templated assembly and electrode attachment of a conducting silver wire", Nature, 391, 775-778, (1998).
Brus, "Quantum crystallites and nonlinear optics", Appl. Phys. A., 53, 465-474 (1991).
Burwell, "Modified silica gels as adsorbents and catalysts", Chemical Technology, 4, 370-377 (1974).
Calin, et al. "Frequent deletions and down-regulation of micro-RNA genes miR15 and miR16 at 13q14 in chronic lymphocytic leukemia." Proc. Natl. Acad. Sci. U. S. A. 99, 15524-15529 (2002).
Chai, et al., "A novel electrochemiluminescence strategy for ultrasensitive DNA assay using luminol functionalized gold nanoparticles multi-labeling and amplification of gold nanoparticles and biotin-streptavidin system." Chem. Commun. 46, 7560-7562 (2010).
Chen, et al, "Real-time quantification of microRNAs by stem-loop RT-PCR." Nucleic Acids Res. 33 e179 (2005).
Cheng, et al., "Cascade Signal Amplification Strategy for Subattomolar Protein Detection by Rolling Circle Amplification and Quantum Dots Tagging." Anal. Chem. 82, 3337-3342 (2010).
Curtis, et al., "A Morphology-Selective Copper Organosol", Angew. Chem. Int. Ed. Engl., 27, 1530 (1988).
Dong, et al., "MicroRNA: Function, Detection, and Bioanalysis." Chem. Rev. 113, 6207-6233 (2013).
Eltekova and Eltekov, "Adsorption of aromatic compounds from solutions on titanium dioxide and silica" Langmuir, 3, 951-957 (1987).
Esquela-Kerscher, et al., "Oncomirs—microRNAs with a role in cancer." Nat. Rev. Cancer 6, 259-269 (2006).
Gao, et al., "Detection of nucleic acids using enzyme-catalyzed template-guided deposition of polyaniline." Adv. Mater. 19, 602-606 (2007).
Grabar et al., "Preparation and characterization of Au colloid monolayers", Anal. Chem., 67, 735-743 (1995).
Henglein, et al., Absorption Spectrum and Some Chemical Reactions of Colloidal Platinum in Aqueous Solution, J. Phys. Chem., 99, 14129 (1995).
Henglein, "Small-particle research: physicochemical properties of extremely small colloidal metal and semiconductor particles", Chem. Rev., 89, 1861-1873 (1989).
Henglein, "Mechanism of reactions on colloidal microelectrodes and size quantization effects", Top. Curr. Chem., 143, 113 (1988).
Hickman et al., "Combining spontaneous molecular assembly with microfabrication to pattern surfaces: selective binding of isonitriles to platinum microwires and characterization by electrochemistry and surface spectroscopy", J. Am. Chem. Soc., 111, 7271-7272 (1989).
Hill, et al., "Nonenzymatic detection of bacterial genomic DNA using the bio bar code assay." Anal. Chem. 79, 9218-9223 (2007).
Hong, et al., "Direct detection of circulating microRNAs in serum of cancer patients by coupling protein-facilitated specific enrichment and rolling circle amplification." Chem. Commun. 50, 3292-3295 (2014).
Hu, et al., "Electrochemical DNA Biosensor Based on Nanoporous Gold Electrode and Multifunctional Encoded DNA-Au Bio Bar Codes." Analytical Chemistry 80, 9124-9130 (2008).
Huang, et al., "Single-particle placement via self-limiting electrostatic gating." Appl. Phys. Lett. 93, 073110 (2008).
Hubbard, "Electrochemistry of well-defined surfaces", Acc. Chem. Res., 13, 177-184 (1980).
Jia, et al., "Ultrasensitive Detection of microRNAs by Exponential Isothermal Amplification." Angew. Chem.-Int. Edit. 49, 5498-5501 (2010).

(56) References Cited

OTHER PUBLICATIONS

Kazane, et al., "Site-specific DNA-antibody conjugates for specific and sensitive immuno-PCR." Proc. Natl. Acad. Sci. U. S. A. 109, 3731-3736 (2012).

Kim, et al., "Microarray-Based Multiplexed Scanometric Immunoassay for Protein Cancer Markers Using Gold Nanoparticle Probes." Analytical Chemistry 81, 9183-9187 (2009).

Lee, et al., "Adsorption of ordered zirconium phosphonate multilayer films on silicon and gold surfaces", J. Phys. Chem., 92, 2597-2601 (1988).

Lee, et al., "SPR imaging measurements of 1-D and 2-D DNA microarrays created from microfluidic channels on gold thin films." Analytical Chemistry 73, 5525-5531 (2001).

Lu, et al., "MicroRNA expression profiles classify human cancers." Nature 435, 834-838 (2005).

Ma, et al., "Electrostatic funneling for precise nanoparticle placement: A route to wafer-scale integration." Nano Lett. 7, 439-445 (2007).

Ma, et al., "Attomolar DNA detection with chiral nanorod assemblies." Nature Communications 4, 2689 (2013).

Maoz and Sagiv, "Penetration-controlled reactions in organized monolayer assemblies. 1. Aqueous permanganate interaction with monolayer and multilayer films of long-chain surfactants", Langmuir, 3, 1034 (1987).

Mashimo, et al., "Detection of small RNA molecules by a combination of branched rolling circle amplification and bioluminescent pyrophosphate assay." Analytical and Bioanalytical Chemistry 401, 221-227 (2011).

Massart, R., "Preparation of aqueous magnetic liquids in alkaline and acidic media", IEEE Transactions on Magnetics, 17, 1247-1248 (1981).

Matteucci and Caruthers, "Synthesis of deoxyoligonucleotides on a polymer support", J. Am. Chem. Soc., 103, 3185-3191 (1981).

Mucic et al., "Synthesis and characterization of DNA with ferrocenyl groups attached to their 5'-termini: electrochemical characterization of a redox-active nucleotide monolayer", Chem. Commun. 555-557 (1996).

Munge, et al., "Multiple enzyme layers on carbon nanotubes for electrochemical detection down to 80 DNA copies." Anal. Chem. 77, 4662-4666 (2005).

Nam, et al., "Bio-bar-code-based DNA detection with PCR-like sensitivity." J. Am. Chem. Soc. 126, 5932-5933 (2004).

Nam, et al., "Nanoparticle-based bio-bar codes for the ultrasensitive detection of proteins." Science 301, 1884-1886 (2003).

Nicoloso, et al., "MicroRNAs—the micro steering wheel of tumour metastases." Nat. Rev. Cancer 9, 293-302 (2009).

Nuzzo et al., "Spontaneously organized molecular assemblies. 3. Preparation and properties of solution adsorbed monolayers of organic disulfides on gold surfaces", J. Am. Chem. Soc., 109, 2358-2368 (1987).

Olshaysky et al., "Organometallic synthesis of gallium-arsenide crystallites, exhibiting quantum confinement", J. Am. Chem. Soc., 112, 9438-9439 (1990).

Onclin, et al., "Engineering silicon oxide surfaces using self-assembled monolayers." Angew. Chem. Int. Ed. 44, 6282-6304 (2005).

Park, et al., "Signal Amplification via Biological Self-Assembly of Surface-Engineered Quantum Dots for Multiplexed Subattomolar Immunoassays and Apoptosis Imaging." Acs Nano 7, 9416-9427 (2013).

Park, et al., "Array-Based Electrical Detection of DNA with Nanoparticle Probes." Science 295, 1503-1506 (2002).

Rakitin, et al., "Metallic Conduction through Engineered DNA: DNA Nanoelectronic Building Blocks", Phys. Rev. Lett., 86(16), 3670-3673, (2001).

Read, et al. The genome sequence of Bacillus anthracis Ames and comparison to closely related bacteria. Nature 423, 81-86 (2003).

Romand, et al., "Usefulness of quantitative polymerase chain reaction in amniotic fluid as early prognostic marker of fetal infection with Toxoplasma gondii." American Journal of Obstetrics and Gynecology 190, 797-802 (2004).

Saiki, et al., "Enzymatic Amplification of Beta-Globin Genomic Sequences and Restriction Site Analysis for Diagnosis of Sickle-Cell Anemia." Science 230, 1350-1354 (1985).

Sano, et al., "Immuno-PCR: Very Sensitive Antigen Detection by Means of Specific Antibody-DNA Conjugates." Science 258, 120-122 (1992).

Shiddiky, et al., "Hydrazine-catalyzed ultrasensitive detection of DNA and proteins." Anal. Chem. 79, 6886-6890 (2007).

Smith, et al., "Patterning self-assembled monolayers." Prog. Surf. Sci. 75, 1-68 (2004).

Soriaga and Hubbard, "Determination of the orientation of aromatic molecules adsorbed on platinum electrodes. The effect of solute concentration", J. Am. Chem. Soc., 104, 3937-3945 (1982).

Stoeva, et al., "Multiplexed detection of protein cancer markers with biobarcoded nanoparticle probes." J. Am. Chem. Soc. 128, 8378-8379 (2006).

Stoeva, et al., "Multiplexed DNA detection with biobarcoded nanoparticle probes." Angew. Chem.-Int. Edit. 45, 3303-3306 (2006).

Su, et al., "Identification of quantitative trait loci controlling acute virulence in Toxoplasma gondii." Proceedings of the National Academy of Sciences of the United States of America 99, 10753-10758 (2002).

Taton, et al., "Scanometric DNA Array Detection with Nanoparticle Probes." Science 289, 1757-1760 (2000).

Thaxton, et al., "Nanoparticle-based bio-barcode assay redefines "undetectable" PSA and biochemical recurrence after radical prostatectomy." Proc. Natl. Acad. Sci. U. S. A. 106, 18437-18442 (2009).

Thomsen, et al., "Monitoring endangered freshwater biodiversity using environmental DNA." Molecular Ecology 21, 2565-2573 (2012).

Timmons and Zisman, "Investigation of Fatty Acid Monolayers on Metals by Contact Potential Measurements1", J. Phys. Chem., 69, 984-990 (1965).

Trebitz, et al., "Potential for DNA-based identification of Great Lakes fauna: match and mismatch between taxa inventories and DNA barcode libraries." Sci. Rep. 5, 12162 (2015).

Tricoli, et al., "MicroRNA: Potential for Cancer Detection, Diagnosis, and Prognosis." Cancer Research 67, 4553-4555 (2007).

Ushida et al., "Gallium arsenide nanocrystals prepared in quinoline", J. Phys. Chem., 95, 5382-5384 (1991).

Van Ness, et al., "Isothermal reactions for the amplification of oligonucleotides." Proc. Natl. Acad. Sci. U. S. A. 100, 4504-4509 (2003).

Vora, et al., "Human Infection with a Zoonotic Orthopoxvirus in the Country of Georgia." New England Journal of Medicine 372, 1223-1230 (2015).

Wang and Herron, "Nanometer-sized semiconductor clusters: materials synthesis, quantum size effects, and photophysical properties", J. Phys. Chem., 95, 525 (1991).

Wang, et al., "Sensitive Detection of MicroRNAs with Hairpin Probe-Based Circular Exponential Amplification Assay." Anal. Chem. 84, 7037-7042 (2012).

Wang, et al., "Nanopore-based detection of circulating microRNAs in lung cancer patients." Nat. Nanotechnol. 6, 668-674 (2011).

Wasserman, et al., "Structure and reactivity of alkylsiloxane monolayers formed by reaction of alkyltrichlorosilanes on silicon substrates", Langmuir, 5, 1074 (1989).

Wei, et al., "Using a microfluidic device for 1 ml DNA microarray hybridization in 500s." Nucleic Acids Research 33, e78 (2005).

Weller, "Colloidal Semiconductor Q-Particles: Chemistry in the Transition Region Between Solid State and Molecules", Angew. Chem. Int. Ed. Engl., 32, 41-53 (1993).

Wen, et al., "DNAzyme-Based Rolling-Circle Amplification DNA Machine for Ultrasensitive Analysis of MicroRNA in *Drosophila larva*." Anal. Chem. 84, 7664-7669 (2012).

Whitesides, Proceedings of the Robert A. Welch Foundation 39th Conference on Chemical Research Nanophase Chemistry, Houston, Tex., pp. 109-121 (1995).

(56) References Cited

OTHER PUBLICATIONS

Zanoli, et al., "Functionalized gold nanoparticles for ultrasensitive DNA detection." Analytical and Bioanalytical Chemistry 402, 1759-1771 (2012).
Zhang, et al., "Ultrasensitive assays for proteins." Analyst 132, 724-737 (2007).
Zhang, et al., "Sensitive Detection of microRNA with Isothermal Amplification and a Single-Quantum-Dot-Based Nanosensor." Anal. Chem. 84, 224-231 (2012).
Zhao, et al., "Ultrasensitive DNA detection using highly fluorescent bioconjugated nanoparticles." J. Am. Chem. Soc. 125, 11474-11475 (2003).
Zhou, et al., "Biomineralization-Assisted Ultrasensitive Detection of DNA." J. Am. Chem. Soc. 132, 6932-6934 (2010).
Zhou, et al., "A dumbbell probe-mediated rolling circle amplification strategy for highly sensitive microRNA detection." Nucleic Acids Res. 38 e156 (2010).
Zhu, et al., "How to Prepare Reproducible, Homogeneous, and Hydrolytically Stable Aminosilane-Derived Layers on Silica." Langmuir 28, 416-423 (2012).
Zuo, et al., "Sensitive and Selective Amplified Fluorescence DNA Detection Based on Exonuclease III-Aided Target Recycling." J. Am. Chem. Soc. 132, 1816-1818 (2010).
International Preliminary Report on Patentability issued for International Application No. PCT/US2017/013319, dated Jul. 26, 2018.

\* cited by examiner

SINGLE-PARTICLE BRIDGE ASSAY FOR AMPLIFICATION-FREE ELECTRICAL DETECTION OF ULTRALOW-CONCENTRATION BIOMOLECULES AND NON-BIOLOGICAL MOLECULES

CROSS REFERENCE TO RELATED APPLICATIONS

This application is a national stage application filed under 35 U.S.C. § 371 of PCT/US2017/013319 filed Jan. 13, 2017, which claims the benefit of U.S. Provisional Patent Application Ser. No. 62/279,385 filed Jan. 15, 2016, each of which are expressly incorporated herein by reference.

STATEMENT REGARDING FEDERALLY SPONSORED RESEARCH

This invention was made with Government Support under Grant No. ECCS-0925997 awarded by the National Science Foundation. The Government has certain rights to the invention.

FIELD

The invention relates generally to devices, systems, compositions, and methods for the detection of oligonucleotides, nucleic acids, antigens, antibodies, peptides, proteins, and non-biological molecules.

BACKGROUND

Ability to detect low concentrations of oligonucleotides, nucleic acids, antigens, antibodies, peptides, proteins, or non-biological molecules plays an important role in diagnosing diseases, detecting pathogens, analyzing forensic samples and advancing life science research. Detection of DNA and/or RNA of a specific sequence can identify genetic diseases, lethal bio-warfare agents and pathogens in humans, animals, foods, and the environment. The capability of detecting specific RNA molecules and their expression levels can be used for diagnosis and prognosis of various human cancers. Detection of proteins, antigens, or antibodies can identify infectious diseases and can also detect biomarkers of cancers or other diseases. Detection of non-biological molecules can identify the presence of explosives for protection against terrorist attacks. For all these needs, having a detection technique that is highly sensitive, specific, portable, and inexpensive would be highly beneficial.

Current commonly accepted methods for low-concentration oligonucleotide/nucleic acids detection usually rely on some type of amplification procedure. These include enzymatic target amplifications using polymerase chain reaction (PCR), rolling circle amplifications (RCA) using DNA and RNA polymerases, barcode-DNA amplifications, exponential amplification reactions (EXPAR) using isothermal polymerase reaction and nicking and reporter/probe amplifications. However, amplification-based oligonucleotide detections inevitably involve many process steps, and therefore are time-consuming and generally require lab space, expensive instrumentation and reagents, and trained personnel. Importantly, the amplification procedure is more often encountered by intrinsic limitations. For example, amplification of microRNAs (miRNAs) using the reverse transcription PCR (RT-PCR) is prone to errors due to the short length of the miRNA (18-25 nucleotides in length), which imposes limitations on the primer design and associated PCR amplification. Detection of low levels of antigens or antibodies is difficult due to the lack of assays for amplification of proteins. Current methods for detecting the presence of non-biologicals (for example, explosives) include vapor detection, bulk detection, and tagging. However, all of these methods have significant difficulties dependent upon the nature of the signature that is detected. Considering these, it would be highly desirable to have a detection method that is sensitive and does not rely on any amplification procedure, either enzymatic or non-enzymatic. Processes that permit the rapid detection of oligonucleotides, nucleic acids, antigens, antibodies, peptides, proteins, or non-biological molecules at very low concentrations are also desirable.

The devices, systems, methods, and compositions disclosed herein address these and other needs.

SUMMARY

Disclosed herein are devices, systems, compositions and methods for the detection of target molecules, such as oligonucleotides, nucleic acids, antigens, proteins, antibodies, or non-biological molecules using capture nanoparticles capable of forming a single-particle bridge with probe nanoparticles, leading to the production of a detectable electrical current. The disclosed devices, compositions, and methods allow the electrical detection of even a single target molecule with formation of a single-particle bridge (termed the "single-particle bridge assay" or "SPBA").

The single-particle bridge assay (SPBA) disclosed herein can provide at least the following benefits:
1. Extremely sensitive: a single target molecule can be electrically detected through the formation of a single-particle bridge between the source and drain electrodes;
2. Fast: detection time is reduced because a single target molecule migrates only for a short distance and for a short time before it is captured by any of the millions (or billions) of capture nanoparticles; in addition, there is no need for an additional amplification step (e.g., PCR);
3. Portable: the kit size can be made smaller than a person's thumb and can be used in remote places (e.g. where medical facilities are not available, including battle fields, rural areas, etc.);
4. Easy communication: the test results can be sent via smart phones, WiFi networks, etc.;
5. Disposable: the devices can be discarded after each individual use;
6. Inexpensive: use of standard manufacturing processes can be used for the rapid production of inexpensive devices and test kits; and/or
7. Multi-disease detection: one kit can simultaneously detect many diseases (e.g., HIV, Ebola, polio, anthrax, etc.).

In one embodiment, the invention is directed to a device comprising:
an electrically-insulating substrate; and
a first detecting unit, comprising:
a source electrode disposed on the electrically-insulating substrate;
a drain electrode;
a dielectric layer;
wherein the dielectric layer is disposed between the source electrode and the drain electrode;
wherein the drain electrode and the dielectric layer comprise an array of holes;

wherein the holes in the drain electrode and the dielectric layer are aligned; and
at least one capture unit, comprising:
a capture nanoparticle;
wherein the capture nanoparticle is in contact with the source electrode; wherein the capture nanoparticle is substantially centered in the holes of the drain electrode and the dielectric layer; and wherein the capture nanoparticle is a metal, semiconductor, or magnetic nanoparticle.

In one embodiment, the invention is directed to devices described herein, further comprising:
a probe nanoparticle;
wherein the probe nanoparticle forms a nanoparticle-bridge conjugate with the capture nanoparticle in the presence of a target molecule;
wherein the probe nanoparticle in the nanoparticle-bridge conjugate provides an electrical path between the capture nanoparticle and the drain electrode.

In one embodiment, the invention is directed to devices described herein, further comprising:
a first oligonucleotide target;
wherein the capture nanoparticle comprises a first single-stranded oligonucleotide having a first nucleotide sequence complementary to a portion of the first oligonucleotide target; and
a plurality of probe nanoparticles;
wherein the probe nanoparticles comprise at least one nanoparticle and a probe oligonucleotide complementary to at least a portion of the first oligonucleotide target different than the portion complementary to the first nucleotide sequence; and
wherein the probe nanoparticle is a metal, semiconductor, or magnetic nanoparticle.

In one embodiment, the invention is directed to devices described herein, further comprising:
a polypeptide target;
wherein the capture nanoparticle comprises a first antibody having an affinity for the polypeptide target; and wherein the capture nanoparticle is a metal, semiconductor, or magnetic nanoparticle; and
a plurality of probe nanoparticles;
wherein the probe nanoparticles comprise at least one nanoparticle and a second antibody capable of binding an unbound portion of the polypeptide target; and
wherein the probe nanoparticle is a metal, semiconductor, or magnetic nanoparticle.

In one embodiment, the invention is directed to devices described herein, further comprising:
a target molecule;
wherein the capture nanoparticle comprises a capture molecule having an affinity for the target molecule; and wherein the capture nanoparticle is a metal, semiconductor, or magnetic nanoparticle; and
a plurality of probe nanoparticles;
wherein the probe nanoparticles comprise at least one nanoparticle and a probe molecule capable of binding an unbound portion of the target molecule; and
wherein the probe nanoparticle is a metal, semiconductor, or magnetic nanoparticle.

In another embodiment, the invention is directed to devices described herein, further comprising:
a plurality of second detecting units, each second detecting unit comprising:
an electrically-insulating substrate;
a source electrode disposed on the electrically-insulating substrate;
a drain electrode; and
a dielectric layer;
wherein the dielectric layer is disposed between the source electrode and the drain electrode;
wherein the drain electrode and the dielectric layer comprise an array of holes;
wherein the holes in the drain electrode and the dielectric layer are aligned; and
at least one capture unit, comprising:
a capture nanoparticle;
wherein the capture nanoparticle is in contact with the source electrode; wherein the capture nanoparticle is substantially centered in the holes of the drain electrode and the dielectric layer; and wherein the capture nanoparticle is a metal, semiconductor, or magnetic nanoparticle.

In one embodiment, the invention is directed to a method of detecting nucleic acid hybridization, comprising:
providing a device described herein;
providing a first oligonucleotide target;
wherein the capture nanoparticle comprises a first single-stranded oligonucleotide having a first nucleotide sequence complementary to a portion of the first oligonucleotide target;
wherein the first oligonucleotide target hybridizes a portion of the first single-stranded oligonucleotide thereby leaving an unhybridized portion of the first oligonucleotide target;
providing a plurality of first probe nanoparticles under hybridizing conditions;
wherein the first probe nanoparticles comprise at least one nanoparticle and a probe oligonucleotide complementary to the unhybridized portion of the first oligonucleotide target;
wherein the nanoparticle in the first probe nanoparticle is a metal, semiconductor, or magnetic nanoparticle;
applying a voltage drop across the electrodes; and
measuring a change in conductivity, resistivity, capacitance, or impedance across the electrodes at known locations to determine complementarity of the first oligonucleotide target to the first single-stranded oligonucleotide and to determine complementarity of the first oligonucleotide target to the probe oligonucleotide.

In one embodiment, disclosed herein is a method of detecting a polypeptide (for example, a protein, antigen, or protein-antibody interaction), comprising:
providing a device described herein;
wherein the capture nanoparticle is comprised of a plurality of first antibodies attached to the nanoparticle; and wherein the capture nanoparticle is a metal, semiconductor, or magnetic nanoparticle;
providing a polypeptide target;
wherein the first antibodies have an affinity to a portion of the polypeptide target;
providing a plurality of first probe nanoparticles under hybridizing conditions;
wherein the first probe nanoparticles comprise at least one nanoparticle and a second antibody capable of binding an unbound portion of the polypeptide target;
wherein the probe nanoparticle is a metal, semiconductor, or magnetic nanoparticle;
applying a voltage drop across the electrodes; and
measuring a change in conductivity, resistivity, capacitance, or impedance across the electrodes at known locations to determine binding of the polypeptide target to the first antibodies and to determine binding of the polypeptide target to the second antibodies.

In one embodiment, disclosed herein is a method of detecting a non-biological molecule (for example, an explosive such as TNT), comprising:

providing a device described herein;

wherein the capture nanoparticle is comprised of a plurality of first molecules attached to the nanoparticle; and wherein the capture nanoparticle is a metal, semiconductor, or magnetic nanoparticle;

providing a target molecule;

wherein the first molecules have an affinity to a portion of the target molecule;

providing a plurality of first probe nanoparticles under hybridizing conditions;

wherein the first probe nanoparticles comprise at least one nanoparticle and a probe molecule capable of binding an unbound portion of the target molecule;

wherein the probe nanoparticle is a metal, semiconductor, or magnetic nanoparticle;

applying a voltage drop across the electrodes; and measuring a change in conductivity, resistivity, capacitance, or impedance across the electrodes at known locations to determine binding of the target molecule to the first capture molecule and to determine binding of the target molecule to the probe molecule.

BRIEF DESCRIPTION OF THE DRAWINGS

The accompanying figures, which are incorporated in and constitute a part of this specification, illustrate several aspects described below.

DETAILED DESCRIPTION

Figure 1A:
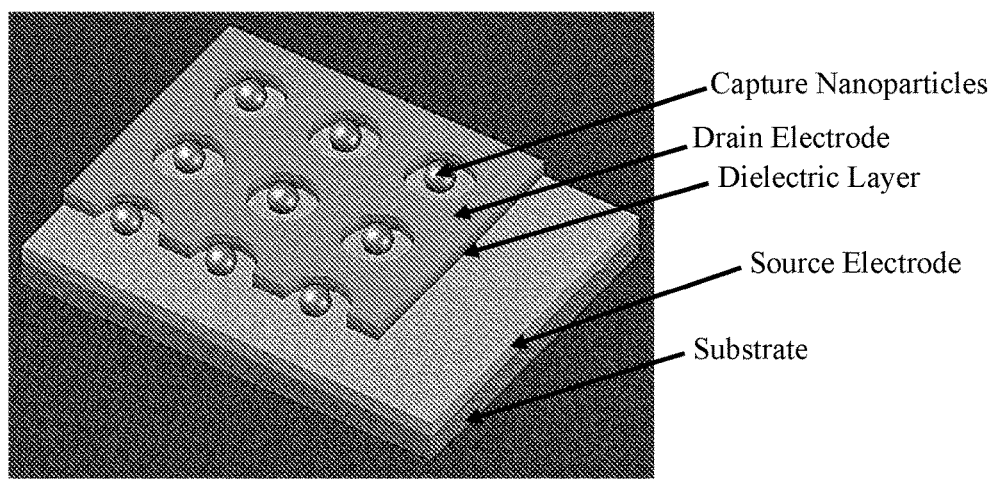
FIG. 1A shows a schematic of the single-particle bridge assay (SPBA) device set up prior to the detection of the oligonucleotide target. The capture nanoparticles (C-NPs) are electrostatically funneled into the center locations of the circular holes of the drain electrode and dielectric layer. The drain electrode is electrically separated from the source electrode by a dielectric layer. The capture nanoparticle is in contact with the source electrode.

Disclosed herein are devices, systems, compositions, and methods for the detection of target molecules, e.g., oligonucleotides, nucleic acids, antigens, proteins, antibodies, or non-biological molecules using capture nanoparticles capable of forming a single-particle bridge with probe nanoparticles, leading to the production of a detectable electrical current. The disclosed devices, compositions, and methods can allow the electrical detection of even a single target molecule with formation of a single-particle bridge (termed the "single-particle bridge assay" or "SPBA"), without the need for an amplification step.

Reference will now be made in detail to the embodiments of the invention, examples of which are illustrated in the drawings and the examples. This invention may, however, be embodied in many different forms and should not be construed as limited to the embodiments set forth herein. In addition and as will be appreciated by one of skill in the art, the invention may be embodied as a product, method, system or process.

Unless defined otherwise, all technical and scientific terms used herein have the same meaning as commonly understood to one of ordinary skill in the art to which this invention belongs. The following definitions are provided for the full understanding of terms used in this specification.

Terminology

As used herein, the article "a," "an," and "the" means "at least one," unless the context in which the article is used clearly indicates otherwise.

As used herein, the term "nucleic acid" as used herein means a polymer composed of nucleotides, e.g. deoxyribonucleotides or ribonucleotides.

As used herein, the terms "ribonucleic acid" and "RNA" as used herein mean a polymer composed of ribonucleotides.

As used herein, the terms "deoxyribonucleic acid" and "DNA" as used herein mean a polymer composed of deoxyribonucleotides.

As used herein, the term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

As used herein, the term "polynucleotide" refers to a single or double stranded polymer composed of nucleotide monomers of generally greater than 100 nucleotides in length and up to about 8,000 or more nucleotides in length.

As used herein, "polypeptide" refers to a compound made up of a single chain of D- or L-amino acids or a mixture of D- and L-amino acids joined by peptide bonds.

As used herein, "aptamer" refers to a molecule (for example, a nucleic acid or a polypeptide) that can selectively bind a target.

As used herein, the term "complementary" refers to the topological compatibility or matching together of interacting surfaces of a probe molecule and its target. Thus, the target and its probe can be described as complementary, and furthermore, the contact surface characteristics are complementary to each other.

As used herein, the term "hybridization" refers to a process of establishing a non-covalent, sequence-specific interaction between two or more complementary strands of nucleic acids into a single hybrid, which in the case of two strands is referred to as a duplex.

As used herein, the term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

As used herein, the term "melting" refers to the denaturation of a double-stranded nucleic acid sequence due to high temperatures, resulting in the separation of the double strand into two single strands by breaking the hydrogen bonds between the strands.

As used herein, the term "capture" refers to the ability of an immobilized molecule to be recognized by a particular target.

As used herein, the term "target" refers to a molecule that has an affinity for a given probe. Targets may be naturally-occurring or man-made molecules. Also, they can be employed in their unaltered state or as aggregates with other species.

As used herein, the term "biological chip," "chip", or "biosensor" refers to a substrate having a surface to which one or more arrays of probes is attached.

As used herein, the term "wafer" refers to a substrate having a surface to which a plurality of probe arrays are attached. On a wafer, the arrays are physically separated by a distance of at least about a millimeter, so that individual chips can be made by dicing a wafer or otherwise physically separating the array into units having a probe array.

As used herein, the phrase "perfectly complementary nucleotide sequences" refers to a nucleic acid duplex wherein the two nucleotide strands match according to the Watson-Crick base pair principle, i.e., A-T and C-G pairs in DNA:DNA duplex and A-U and C-G pairs in DNA:RNA or RNA:RNA duplex, and there is no deletion or addition in each of the two strands.

As used herein, the phrase "substantially uniform thickness" with reference to the dielectric layer of the invention refers to a dimension that varies by less than about 20%, preferably less than about 10%, and more preferably less than about 5%, over the area covered by the layer.

As used herein, the phrase "substantially centered" is used with reference to the capture unit of the invention and means that the location of the midpoint of the nanoparticle in no more than about 30%, preferably less than about 20%, and more preferably less than about 10%, away from the center of each of the circular holes in the drain electrode and the circular holes of the dielectric layer; or the location of the midpoint of the nanowire in no more than about 30%, preferably less than about 20%, and more preferably less than about 10%, away from the center line of each of the rectangular holes in the drain electrode and the rectangular holes of the dielectric layer.

As used herein, the phrase "comprise an array of holes" means that a layer of the device (for example, the drain electrode or the dielectric layer) contains a large number of holes (of any shape, for example, circular or rectangular) that are of sufficient size such that a capture nanoparticle (or nanowire) will not come into contact with the edges of the hole, when the capture nanoparticle (or nanowire) is placed in the center of the hole. In certain embodiments, the array of holes (of any shape, for example, circular or rectangular) are arrayed in a grid format, such that the holes are substantially the same distance apart from each other As used herein, the phrase "comprise an array of circular holes" means that a layer of the device (for example, the drain electrode or the dielectric layer) contains a large number of substantially circular holes that are of sufficient size such that a capture nanoparticle will not come into contact with the edges of the circular hole, when the capture nanoparticle is placed in the center of the circular hole. In certain embodiments, the array of circular holes are arrayed in a grid format, such that the circular holes are substantially the same distance apart from each other.

As used herein, the phrase "comprise an array of rectangular holes" means that a layer of the device (for example, the drain electrode or the dielectric layer) contains a large number of substantially rectangular holes that are of sufficient size such that a capture nanoparticle (i.e. nanowire) will not come into contact with the edges of the rectangular hole, when the capture nanoparticle is placed in the center of the rectangular hole. In certain embodiments, the array of rectangular holes are arrayed in a grid format, such that the rectangular holes are substantially the same distance apart from each other.

As used herein, the term "aligned," when used in reference to the drain electrode and dielectric layer, means that the shape of the drain electrode is transferred to dielectric layer, and that the holes of the drain electrode and the holes of the dielectric layer are substantially aligned.

As used herein, the term "dielectric" refers to an electrical insulating material that may be polarized by the action of an applied electric field. When a dielectric material is placed in electric field, electric charges do not flow through the material, as in conductor, but only slightly shift from their average equilibrium positions causing dielectric polarization: positive charges are displaced along the field and negative charges shift in the opposite direction. This creates an internal electric field which partly compensates the external field inside the dielectric material.

As used herein, the term "portion", refers to less than the entire sequence of nucleic acid bases forming the oligonucleotide (when used in reference to an oligonucleotide) or less than entire sequence of amino acids forming the polypeptide (when used in reference to a polypeptide) or less than entire molecule forming the target molecule (when used in reference to a non-biological molecule). If a portion of oligonucleotide target hybridizes (due to complementarity) with the single-stranded oligonucleotide (or single-stranded portion of an oligonucleotide) in the capture unit, then the remaining portion of the oligonucleotide target will be available to hybridize with the probe nanoparticles. If a portion of a polypeptide target binds (due to binding specificity) with a first antibody in the capture unit, then the remaining portion of the polypeptide target will be available to specifically bind with the probe nanoparticles. If a portion of a target molecule binds (due to binding) with a first molecule in the capture unit, then the remaining portion of the target molecule will be available to specifically bind with the probe nanoparticles.

As used herein, the term "nanoparticle" refers to any nano-scale or micro-scale object or entity, including, but not limited to tube, rod (wire), disk, hollow sphere, solid sphere, and like. Nanoparticles are not required to be spherical in shape. The dimension of the nanoparticle is typically in the range of a few nanometers to hundreds of nanometers, but could be as large as hundreds of micrometers or as small as less than one nanometer.

As used herein, the term "capture nanoparticle" refers to any nano-scale or micro-scale object or entity, including, but not limited to tube, rod (wire), disk, hollow sphere, solid sphere, and like. Capture nanoparticles are not required to be spherical in shape. Capture nanoparticles can be positioned on top of the source electrode, or can be embedded in the source electrode fully or partially. The dimension of the nanoparticle is typically in the range of a few nanometers to hundreds of nanometers, but could be as large as hundreds of micrometers or as small as less than one nanometer.

Devices

In one embodiment, the invention is directed to a device comprising:

an electrically-insulating substrate; and
a first detecting unit, comprising:
a source electrode disposed on the electrically-insulating substrate;
a drain electrode;
a dielectric layer;
wherein the dielectric layer is disposed between the source electrode and the drain electrode;
wherein the drain electrode and the dielectric layer comprise an array of holes;
wherein the holes in the drain electrode and the dielectric layer are aligned; and
at least one capture unit, comprising:
a capture nanoparticle;
wherein the capture nanoparticle is in contact with the source electrode; wherein the nanoparticle is substantially centered in the holes of the drain electrode and the dielectric layer; and wherein the capture nanoparticle is a metal, semiconductor, or magnetic nanoparticle.

In one embodiment, the invention is directed to devices described herein, further comprising:

a probe nanoparticle;
wherein the probe nanoparticle forms a nanoparticle-bridge conjugate with the capture nanoparticle in the presence of a target molecule;
wherein the probe nanoparticle in the nanoparticle-bridge conjugate provides an electrical path between the capture nanoparticle and the drain electrode.

In one embodiment, the invention is directed to devices described herein, further comprising:

a first oligonucleotide target;
wherein the capture nanoparticle comprises a first single-stranded oligonucleotide having a first nucleotide sequence complementary to a portion of the first oligonucleotide target; and
a plurality of probe nanoparticles;
wherein the probe nanoparticles comprise at least one nanoparticle and a probe oligonucleotide complementary to at least a portion of the first oligonucleotide target different than the portion complementary to the first nucleotide sequence; and
wherein the probe nanoparticle is a metal, semiconductor, or magnetic nanoparticle.

In one embodiment, the invention is directed to devices described herein, further comprising:

a polypeptide target;
wherein the capture nanoparticle comprises a first antibody having an affinity for the polypeptide target; wherein the capture nanoparticle is a metal, semiconductor, or magnetic nanoparticle; and
a plurality of probe nanoparticles;
wherein the probe nanoparticles comprise at least one nanoparticle and a second antibody capable of binding an unbound portion of the polypeptide target; and
wherein the probe nanoparticle is a metal, semiconductor, or magnetic nanoparticle.

In one embodiment, the invention is directed to devices described herein, further comprising:

a target molecule;
wherein the capture nanoparticle comprises a capture molecule having an affinity for the target molecule; and wherein the capture nanoparticle is a metal, semiconductor, or magnetic nanoparticle; and
a plurality of probe nanoparticles;
wherein the probe nanoparticles comprise at least one nanoparticle and a probe molecule capable of binding an unbound portion of the target molecule; and wherein the probe nanoparticle is a metal, semiconductor, or magnetic nanoparticle.

In another embodiment, the invention is directed to devices described herein, further comprising:

a plurality of second detecting units, each second detecting unit comprising:

an electrically-insulating substrate;

a source electrode disposed on the electrically-insulating substrate;

a drain electrode; and a dielectric layer;

wherein the dielectric layer is disposed between the source electrode and the drain electrode;

wherein the drain electrode and the dielectric layer comprise an array of holes;

wherein the holes in the drain electrode and the dielectric layer are aligned; and at least one capture unit, comprising:

a capture nanoparticle;

wherein the capture nanoparticle is in contact with the source electrode; and wherein the capture nanoparticle is substantially centered in the holes of the drain electrode and the dielectric layer.

In certain embodiments of the invention, the nanoparticle is a metal, semiconductor, or magnetic nanoparticle.

In one embodiment, the invention is directed to devices described herein, further comprising:

a first oligonucleotide target;

wherein the capture nanoparticle comprises a first single-stranded oligonucleotide having a first nucleotide sequence complementary to a portion of the first oligonucleotide target; and wherein the capture nanoparticle is a metal, semiconductor, or magnetic nanoparticle; and a plurality of probe nanoparticles;

wherein the probe nanoparticles comprise at least one nanoparticle and a probe oligonucleotide complementary to at least a portion of the first oligonucleotide target different than the portion complementary to the first nucleotide sequence;

wherein the probe nanoparticle is a metal, semiconductor, or magnetic nanoparticle;

wherein the capture nanoparticle, the first oligonucleotide target, and probe nanoparticles form a nanoparticle-bridge conjugate; and wherein the probe nanoparticle in the nanoparticle-bridge conjugate provides an electrical path between the capture nanoparticle and the drain electrode.

In one embodiment, the invention is directed to devices described herein, further comprising:

a polypeptide target;

wherein the capture nanoparticle comprises a first antibody having an affinity for the polypeptide target; and wherein the capture nanoparticle is a metal, semiconductor, or magnetic nanoparticle; and a plurality of probe nanoparticles;

wherein the probe nanoparticles comprise at least one nanoparticle and a second antibody capable of binding an unbound portion of the polypeptide target;

wherein the probe nanoparticle is a metal, semiconductor, or magnetic nanoparticle;

wherein the capture nanoparticle, the polypeptide target, and probe nanoparticles form a nanoparticle-bridge conjugate; and wherein the probe nanoparticle in the nanoparticle-bridge conjugate provides an electrical path between the capture nanoparticle and the drain electrode.

In one embodiment, the invention is directed to devices described herein, further comprising:

a target molecule;

wherein the capture nanoparticle comprises a capture molecule having an affinity for the target molecule; and wherein the capture nanoparticle is a metal, semiconductor, or magnetic nanoparticle; and a plurality of probe nanoparticles;

wherein the probe nanoparticles comprise at least one nanoparticle and a probe molecule capable of binding an unbound portion of the target molecule;

wherein the probe nanoparticle is a metal, semiconductor, or magnetic nanoparticle;

wherein the capture nanoparticle, the target molecule, and probe nanoparticles form a nanoparticle-bridge conjugate; and wherein the probe nanoparticle in the nanoparticle-bridge conjugate provides an electrical path between the capture nanoparticle and the drain electrode.

In one embodiment, the nanoparticle is spherical in shape. In one embodiment, the nanoparticle is in the shape of a wire or rod (i.e. a nanowire).

In one embodiment, the holes are circular in shape. In one embodiment, the holes are rectangular in shape.

Electrically-Insulating Substrates

The devices of the invention include an electrically-insulating substrate. The substrate is preferably flat but may take on a variety of alternative surface configurations. For instance, the substrate may be any electrically insulating material. Suitable substrates include, but are not limited to, functionalized glass, Si, Ge, GaAs, GaN, GaP, $SiO_2$, $SiN_4$, modified silicon, semiconductor-on-insulator (SOI), silicon carbide, diamond thin film or any one of a wide variety of gels or polymers such as (poly)tetrafluoroethylene, (poly)vinylidenedifluoride, polystyrene, polycarbonate, polypropylene, or combinations thereof. As is known to those having skill in the art, the substrate may include one or more heteroepitaxial and/or homoepitaxial layers on the substrate. The substrate may be deposited by chemical vapor deposition. Other substrate materials and deposition methods will be readily apparent to those of skill in the art upon review of this disclosure. In one embodiment, the substrate is flat glass or silica with a silicon dioxide layer grown on the surface to provide electrical insulation.

In certain embodiments of the invention, the electrically-insulating substrate is silicon, silicon dioxide, or a combination thereof. In certain embodiments of the invention, the electrically-insulating substrate comprises more than one layer.

Electrodes

In certain embodiments of the invention, the source and drain electrodes comprise a metal selected from the group consisting of gold, chromium, silver, titanium, copper, Mo, W, Si, GaAs, and InP, or a combination thereof. In certain embodiments of the invention, the source and drain electrodes comprise a metal selected from the group consisting of gold, chromium, silver, titanium, copper, or a combination thereof. In one embodiment, the source electrode is selected from the group consisting of Cr, Ti, Mo, W, Si, GaAs, and InP. In one embodiment, the source electrode is chromium (Cr). In one embodiment, the drain electrode is selected from the group consisting of gold, silver, titanium, and copper. In one embodiment, the drain electrode is gold.

The source and drain electrodes are preferably comprised of different metals in order to allow the first self-assembled monolayer (positively charged) and the second self-assembled monolayer (negatively charged) to attach the source and drain electrodes, respectively.

The structure may be covered with microfluidic channels. The electrical isolation may be achieved by sequential and automated measurement of each pair of electrodes.

In certain embodiments, nanopatterns may be made on an oxidized silicon wafer using e-beam lithography (EBL). The EBL patterns may be used to fabricate the stamp for the nanoelectrode fabrication. The EBL patterns may be used to remove silicon dioxide and then silicon from the non-patterned areas using deep reactive ion etching (DRIE). Silicon dioxide acts as a hard mask during the process, resulting in a high aspect ratio nano-scale linear island features in silicon having the same dimensions as required the nanogap electrodes. The wafer may act as a stamping mask for nanoimprint lithography (NIL). In NIL, a polymer layer is spun on the wafer and a stamping wafer is compressed on the polymer to transfer the pattern. One stamp can be used multiple times and one stamping takes a few minutes to transfer the nano-scale patterns in the polymer. Standard lift-off process may be carried out to create the metal lines at the nanoscale from these stamp-defined patterns. In certain embodiments of the lift-off process, metal stays only in the NIL transferred nanoelectrode structure and the remainder of the metal lifts off in an ultra-sonicator assisted solvent soak. The first layer of addressing electrodes/bus may then be using standard optical lithography aligned to the nano-scale metal lines. The second layer of metal lines/bus may be deposited after chemical vapor deposition (CVD) of silicon nitride and reactive ion etch opening of small micron sized windows in the silicon nitride above the nanogap electrodes.

Dielectric Layer

The dielectric layer is comprised of an electrical insulating material that may be polarized by the action of an applied electric field. When a dielectric material is placed in electric field, electric charges do not flow through the material, as in conductor, but only slightly shift from their average equilibrium positions causing dielectric polarization: positive charges are displaced along the field and negative charges shift in the opposite direction. This creates an internal electric field which partly compensates the external field inside the dielectric material.

In one embodiment, the dielectric layer is selected from the group consisting of $SiO_2$, $Si_3N_4$, $HfO_2$, and $Al_2O_3$. In one embodiment, the dielectric layer is $SiO_2$. In one embodiment, the dielectric layer has a substantially uniform thickness.

Self-Assembled Monolayers (SAMs)

The formation of self-assembled monolayers (SAMs) is used to precisely place the capture nanoparticle units. More specifically, first and second self-assembled monolayers, which form an electrostatic funneling (guiding) structure, enable the placement of capture nanoparticles (capture units) in the center of the circular holes of the drain electrode and the circular holes of the dielectric layer. Likewise, the formation of self-assembled monolayers (SAMs) is used to precisely place the capture nanowire units in the center of the (rectangular) holes of the drain electrode and the (rectangular) holes of the dielectric layer.

Passivation: Prior to exposure to target, the first self-assembled monolayer on the dielectric layer can be modified (passivated) to produce different polarity. For example, the positively-charged self-assembled monolayers can be changed so that the terminal group of the molecular layers are terminated by non-polar or negatively charged molecules. This passivation ensures that the target molecules (e.g., DNA, RNA, protein) do not attach to the dielectric surface, thereby increasing the probability that the target molecule finds the surface of capture units the only possible place for hybridization or antigen-antibody reaction.

SAM structures generally comprise an organic or inorganic molecule or compound with a tail group that holds electric charge, such as an amino group (—$NH_2$ with a positive charge) or carboxyl group (—COOH with a negative charge). The molecule selected is not dependent upon a specific chemistry but must be one that has affinity for nanoparticle adhesion and must be capable of forming a monolayer-like structure.

In the device of the invention, the first self-assembled monolayer is attached to and in contact with the source electrode. The second self-assembled monolayer is attached to and in contact with the drain electrode, wherein the second monolayer has a polarity different than the polarity of the first monolayer. In certain embodiments of the invention, the first self-assembled monolayer is positively-charged. In certain embodiments of the invention, the second self-assembled monolayer is negatively-charged or neutral. Differentially treated surfaces, i.e., using two different surface-assembled monolayers, allow the capture nanoparticles to be electrostatically guided and placed onto centers of the circular holes. The surfaces then may be passivated to ensure that target molecules only interact with the capture units and not with the remaining surfaces in the device (allowing detection of extremely low quantities of target molecules, even as low as the molecular level).

In the biosensor of the invention, the presence of oligonucleotide target (T-oligo) molecules leads to, through DNA hybridization, the formation of bridges with the probe nanoparticles (P-NPs) around the C-NPs. The important feature of the approach is that the DNA hybridization is carried out on C-NPs. For this exclusive hybridization to be successful, it is essential that when migrating DNA molecules impinge on any surface except for that of C-NPs, they should not be adsorbed, but returned back into the solution so that they remain available for hybridization. The drain electrode (Au) is functionalized with 16-mercaptohexadecanoic acid (MHA; —COO— terminated; negatively charged), which repel DNA molecules.

In one embodiment, a first self-assembled monolayer is attached to and in contact with the source electrode. In one embodiment, a second self-assembled monolayer is attached to and in contact with the drain electrode. In a further embodiment, the second self-assembled monolayer has a polarity different than the polarity of the first self-assembled monolayer. In one embodiment, the first self-assembled monolayer is 3-aminopropyltriethoxysilane (APTES: $(C_2H_5O)_3$—Si—$(CH_2)_3$—$NH_2$; positively charged with $NH_3^+$ termination). In one embodiment, the second self-assembled monolayer is 16-mercaptohexadecanoic acid (MHA: HS-$(CH_2)_{15}$—COOH; negatively charged with $COO^-$ termination).

Capture Units

The capture units (referred to herein as C-NP) used in the devices, systems, and methods of the invention comprise:
 a capture nanoparticle;
 wherein the capture nanoparticle is in contact with the source electrode; and wherein the capture nanoparticle is substantially centered in the circular holes of the drain electrode and the dielectric layer.

In one embodiment, the nanoparticle is comprised of a plurality of first single-stranded oligonucleotides (also referred to as capture oligonucleotides, or C-oligos) attached to the nanoparticle; wherein the first single-stranded oligonucleotides have a first nucleotide sequence complementary to a portion of a first oligonucleotide target (or T-oligos).

It should be noted that while the capture unit can contain single-stranded oligonucleotide, it may also contain a portion of olignonucleotide that is double-stranded. In one embodiment, at least a portion of the oligonucleotide in the capture unit is single-stranded so that it can function to hybridize with the oligonucleotide target.

In one embodiment, the capture nanoparticle is comprised of a plurality of first antibodies attached to the nanoparticle; wherein the first antibodies have affinity to a portion of a polypeptide target.

Oligonucleotides of defined sequences are used for a variety of purposes in the practice of the invention. Methods of making oligonucleotides of a predetermined sequence are well-known. See, e.g., Sambrook et al., *Molecular Cloning: A Laboratory Manual* (2nd ed. 1989) and F. Eckstein (ed.) *Oligonucleotides and Analogues*, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

In typical diagnostic applications, a solution containing one or more targets to be identified (i.e., samples from patients) contacts the probe array. The targets will bind or hybridize with complementary probe sequences. Accordingly, the probes will be selected to have sequences directed to (i.e., having at least some complementarity with) the target sequences to be detected, e.g., human or pathogen sequences. The probe nanoparticles only hybridize with those probes where there has been a binding event with a target, permitting an electrical current to be detected at known locations. Accordingly, locations at which targets hybridize with complimentary probes can be identified by locating the electrical current in an electrode set. Based on the locations of the electrodes where hybridization occurs, information regarding the target sequences can be extracted. The existence of a mutation may be determined by comparing the target sequence with the wild type.

The nanoparticles, the oligonucleotides, or both are functionalized in order to attach the oligonucleotides to the nanoparticles. Such methods are known in the art. For instance, oligonucleotides functionalized with alkanethiols at their 3'-termini or 5'-termini readily attach to gold nanoparticles. See Whitesides, *Proceedings of the Robert A. Welch Foundation* 39th *Conference On Chemical Research Nanophase Chemistry*, Houston, Tex., pages 109-121 (1995). See also, Mucic et al., *Chem. Commun.* 555-557 (1996), which describes a method of attaching 3' thiol DNA to flat gold surfaces; this method can be used to attach oligonucleotides to nanoparticles. The alkanethiol method can also be used to attach oligonucleotides to other metal, semiconductor, and magnetic colloids and to the other nanoparticles listed above. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, *Chemical Technology*, 4, 370-377 (1974) and Matteucci and Caruthers, *J. Am. Chem. Soc.*, 103, 3185-3191 (1981) for binding of oligonucleotides to silica and glass surfaces, and Grabar et al., *Anal. Chem.*, 67, 735-743 for binding of aminoalkylsiloxanes and for similar binding of mercaptoalkylsiloxanes). Oligonucleotides terminated with a 5' thionucleoside or a 3' thionucleoside may also be used for attaching oligonucleotides to solid surfaces. The following references describe other methods that may be employed to attached oligonucleotides to nanoparticles: Nuzzo et al., *J. Am. Chem. Soc.*, 109, 2358 (1987) (disulfides on gold); Allara and Nuzzo, *Langmuir*, 1, 45 (1985) (carboxylic acids on aluminum); Allara and Tompkins, *J. Colloid Interface Sci.*, 49, 410-421 (1974) (carboxylic acids on copper); Iler, *The Chemistry Of Silica*, Chapter 6, (Wiley 1979) (carboxylic acids on silica); Timmons and Zisman, *J. Phys. Chem.*, 69, 984-990 (1965) (carboxylic acids on platinum); Soriaga and Hubbard, *J. Am. Chem. Soc.*, 104, 3937 (1982) (aromatic ring compounds on platinum); Hubbard, *Acc. Chem. Res.*, 13, 177 (1980) (sulfolanes, sulfoxides and other functionalized solvents on platinum); Hickman et al., *J. Am. Chem. Soc.*, 111, 7271 (1989) (isonitriles on platinum); Maoz and Sagiv, *Langmuir*, 3, 1045 (1987) (silanes on silica); Maoz and Sagiv, *Langmuir*, 3, 1034 (1987) (silanes on silica); Wasserman, et al., *Langmuir*, 5, 1074 (1989) (silanes on silica); Eltekova and Eltekov, *Langmuir*, 3, 951 (1987) (aromatic carboxylic acids, aldehydes, alcohols and methoxy groups on titanium dioxide and silica); Lec, et al., *J. Phys. Chem.*, 92, 2597 (1988) (rigid phosphates on metals).

Oligonucleotides functionalized with a cyclic disulfide are within the scope of this invention. The cyclic disulfides preferably have 5 or 6 atoms in their rings, including the two sulfur atoms. Suitable cyclic disulfides are available commercially or may be synthesized by known procedures. The reduced form of the cyclic disulfides can also be used.

In one embodiment, the optional linker further comprises a hydrocarbon moiety attached to the cyclic disulfide. Suitable hydrocarbons are available commercially, and are attached to the cyclic disulfides. Preferably the hydrocarbon moiety is a steroid residue. Oligonucleotide-nanoparticle conjugates prepared using linkers comprising a steroid residue attached to a cyclic disulfide are stable to thiols (e.g., dithiothreitol used in polymerase chain reaction (PCR) solutions) as compared to conjugates prepared using alkanethiols or acyclic disulfides as the linker. This stability is likely due to the fact that each oligonucleotide is anchored to a nanoparticle through two sulfur atoms, rather than a single sulfur atom. In particular, it is thought that two adjacent sulfur atoms of a cyclic disulfide would have a chelation effect which would be advantageous in stabilizing the oligonucleotide-nanoparticle conjugates. The large hydrophobic steroid residues of the linkers contribute to the stability of the conjugates by screening the nanoparticles from the approach of water-soluble molecules to the surfaces of the nanoparticles.

In view of the foregoing, the two sulfur atoms of the cyclic disulfide should preferably be close enough together so that both of the sulfur atoms can attach simultaneously to the nanoparticle. Most preferably, the two sulfur atoms are adjacent each other. Also, the hydrocarbon moiety should be large so as to present a large hydrophobic surface screening the surfaces of the nanoparticles.

Microfluidic Channels

Assays on biological arrays generally include contacting a probe array with a sample under the selected reaction conditions, optionally washing the well to remove unreacted molecules, and analyzing the biological array for evidence of reaction between target molecules and the probe molecules. These steps involve handling fluids. Microfluidic channels may be used to deliver the liquids to the test sites made from any suitable solid material, such as polydimethylsiloxane. The methods of this invention can automate these steps so as to allow multiple assays to be performed concurrently. Accordingly, this invention can employ automated fluid handling systems for concurrently performing the assay steps in each of the test wells. Fluid handling allows uniform treatment of samples in the test sites. Microtiter robotic and fluid-handling devices are available commercially, for example, from Tecan AG.

The device may be introduced into a holder in the fluid-handling device. This robotic device may be programmed to set appropriate reaction conditions, such as temperature, add samples to the device, incubate the test samples for an appropriate time, remove unreacted samples, wash the wells, add substrates as appropriate and perform detection assays. The particulars of the reaction conditions depend upon the purpose of the assay. For example, in a sequencing assay involving DNA hybridization, standard hybridization conditions are chosen. However, the assay may involve testing whether a sample contains target molecules that react to a probe under a specified set of reaction conditions. In this case, the reaction conditions are chosen accordingly.

DNA Array Chips/Multiplex DNA Sensing

The fabrication of the device of the invention may be carried out within the framework of current complementary metal-oxide-semiconductor (CMOS) fabrication technology. This means that arrays of sensor units can be built on a large scale over an entire wafer in parallel processing.

When this capability is combined with well-established DNA microarray technology (which currently can assay hundreds of thousands of different DNA sequences simultaneously), DNA detection technology leads to multiplex DNA sensing, but with sensitivity of detecting extremely low concentrations of unknown T-oligo molecules. Importantly, the output is an electrical signal, which will have tremendous advantages in data handling over the typical optical (fluorescent) output of current DNA microarray technology.

Systems

In one aspect, the invention is directed to systems, comprising:
  a device described herein;
  a first oligonucleotide target;
  wherein the capture nanoparticle comprises a first single-stranded oligonucleotide having a first nucleotide sequence complementary to a portion of the first oligonucleotide target; and
  a plurality of probe nanoparticles (also referred to herein as the P-NPs);
  wherein the probe nanoparticles comprise at least one nanoparticle and a probe oligonucleotide (also referred to as the P-oligo) complementary to at least a portion of the first oligonucleotide target different than the portion complementary to the first nucleotide sequence; and
  wherein the probe nanoparticle is a metal, semiconductor, or magnetic nanoparticle.

In one aspect, the invention is directed to systems, comprising:
  a device described herein;
  a polypeptide target;
  wherein the capture nanoparticle comprises a first antibody (also referred to as the C-Ab) having an affinity for the polypeptide target; and
  a plurality of probe nanoparticles (referred to herein as the P-NPs);
  wherein the probe nanoparticles comprise at least one nanoparticle and a second antibody (also referred to herein as the P-Ab) capable of binding an unbound portion of the polypeptide target; and
  wherein the probe nanoparticle is a metal, semiconductor, or magnetic nanoparticle.

In one aspect, the invention is directed to systems, comprising:
  a device described herein;
  a target molecule;
  wherein the capture nanoparticle comprises a capture molecule (also referred to as the C-molecule) having an affinity for the target molecule; and
  a plurality of probe nanoparticles (referred to herein as the P-NPs);
  wherein the probe nanoparticles comprise at least one nanoparticle and a probe molecule (also referred to herein as the P-molecule) capable of binding an unbound portion of the target molecule; and
  wherein the probe nanoparticle is a metal, semiconductor, or magnetic nanoparticle.

In other aspects, the invention is directed to systems, comprising:
  a device described herein;
  a plurality of first probe nanoparticles; and
  a plurality of at least one second probe nanoparticles;
  wherein the first probe nanoparticles comprise at least one nanoparticle and a probe oligonucleotide complementary to at least a portion of the first oligonucleotide target different than the portion complementary to the first nucleotide sequence;
  wherein the nanoparticle in the first probe nanoparticle is a metal, semiconductor, or magnetic nanoparticle;
  wherein the at least one second probe nanoparticles comprise at least one nanoparticle and a probe oligonucleotide complementary to at least a portion of the at least one second oligonucleotide target different than the portion complementary to the at least one second nucleotide sequence;
  wherein the nanoparticle in the at least one second probe nanoparticle is a metal, semiconductor, or magnetic nanoparticle;
  wherein the second probe nanoparticles are the same or different from the first probe nanoparticles.

In other aspects, the invention is directed to systems, comprising:
  a device described herein;
  a plurality of first probe nanoparticles; and
  a plurality of at least one second probe nanoparticles;
  wherein the first probe nanoparticles comprise at least one nanoparticle and a second antibody capable of binding an unbound portion of the polypeptide target;
  wherein the nanoparticle in the first probe nanoparticle is a metal, semiconductor, or magnetic nanoparticle;
  wherein the at least one second probe nanoparticles comprise at least one nanoparticle and a third antibody capable of binding an unbound portion of a second polypeptide target;
  wherein the nanoparticle in the at least one second probe nanoparticle is a metal, semiconductor, or magnetic nanoparticle;
  wherein the second probe nanoparticles are the same or different from the first probe nanoparticles.

In another aspect, the invention is directed to systems, comprising:
  a device described herein;
  a plurality of first probe nanoparticles; and
  a plurality of at least one second probe nanoparticles;
  wherein the first probe nanoparticles comprise at least one nanoparticle and a second molecule capable of binding an unbound portion of the target molecule;

wherein the nanoparticle in the first probe nanoparticle is a metal, semiconductor, or magnetic nanoparticle;

wherein the at least one second probe nanoparticles comprise at least one nanoparticle and a third molecule capable of binding an unbound portion of a second target molecule;

wherein the nanoparticle in the at least one second probe nanoparticle is a metal, semiconductor, or magnetic nanoparticle;

wherein the second probe nanoparticles are the same or different from the first probe nanoparticles.

Probe Nanoparticles

In methods for the detection of nucleic acid sequences, in some embodiments the probe nanoparticles comprise at least one nanoparticle (either a metal, semiconductor, or magnetic nanoparticle) and a single-stranded probe oligonucleotide complementary to at least a portion of the first oligonucleotide target different than the portion complementary to the first nucleotide sequence. In certain embodiments, the probe nanoparticles further comprise a linker. While not wishing to be bound by theory, it is believed that the probe nanoparticles hybridize with at least a portion of the first oligonucleotide target different than the portion complementary to the first nucleotide sequence. This hybridization facilitates the movement of electrons, at least partially due to the π-stacking of base pairs of the nucleic acids in the double helix structure, thereby increasing the charge conduction between the source and drain electrodes. In addition, in ambient condition, water menisci form around the area between the capture nanoparticle and the probe nanoparticle, resulting in the charge conduction when a voltage bias is applied between the electrodes. The hybridization of the single-stranded oligonucleotide in the capture unit with complementary targets, and their subsequent hybridization with the probe nanoparticles permits charge transport, thus making electrical detection possible. In addition, there is direct contact between the electrodes due to the hybridization of the probe nanoparticles forming the nanoparticle satellites.

In methods for the detection of proteins (e.g., antigens, enzymes, etc.), the probe nanoparticles of the invention comprise at least one nanoparticle (either a metal, semiconductor, or magnetic nanoparticle) and a second antibody capable of binding an unbound portion of the polypeptide target. In one embodiment, the probe nanoparticle is a metal, semiconductor, or magnetic nanoparticle.

Nanoparticles useful in the practice of the invention include metal (e.g., gold, silver, copper and platinum), semiconductor (e.g., Si, CdSe, CdS, and CdS or CdSe coated with ZnS) and magnetic (e.g., ferromagnetite) materials. In certain embodiments, metal nanoparticles, especially gold nanoparticles, are preferred. The use of semiconductor and magnetic nanoparticles permits the use of the same system for multi-modal detection, including capacitance change, impedance change, or from field effect, for example. Other nanoparticles useful in the practice of the invention include $ZnS$, $ZnO$, $TiO_2$, $AgI$, $AgBr$, $HgI_2$, $PbS$, $Pb\,Se$, $ZnTe$, $CdTe$, $In_2S_3$, $In_2Se_3$, $Cd_3P_2$, $Cd_3As_2$, $InAs$, and $GaAs$. In some embodiments, the size of the nanoparticles can be from about 5 nm to about 150 nm (mean diameter), from about 5 to about 50 nm, or from about 10 to about 30 nm.

Methods of making metal, semiconductor and magnetic nanoparticles are well-known in the art. See, e.g., Schmid, G. (ed.) *Clusters and Colloids* (VCH, Weinheim, 1994); Hayat, M. A. (ed.) *Colloidal Gold: Principles, Methods, and Applications* (Academic Press, San Diego, 1991); Massart, R., *IEEE Transactions On Magnetics*, 17, 1247 (1981); Ahmadi, T. S. et al., *Science*, 272, 1924 (1996); Henglein, A. et al., *J. Phys. Chem.*, 99, 14129 (1995); Curtis, A. C., et al., *Angew. Chem. Int. Ed. Engl.*, 27, 1530 (1988), all of which are incorporated herein by reference.

Methods of making $ZnS$, $ZnO$, $TiO_2$, $AgI$, $AgBr$, $HgI_2$, $PbS$, $PbSe$, $ZnTe$, $CdTe$, $In_2S_3$, $In_2Se_3$, $Cd_3P_2$, $Cd_3As_2$, $InAs$, and $GaAs$ nanoparticles are also known in the art. See, e.g., Weller, *Angew. Chem. Int. Ed. Engl.*, 32, 41 (1993); Henglein, *Top. Curr. Chem.*, 143, 113 (1988); Henglein, *Chem. Rev.*, 89, 1861 (1989); Brus, *Appl. Phys. A.*, 53, 465 (1991); Bahncmann, in *Photochemical Conversion and Storage of Solar Energy* (eds. Pelizetti and Schiavello 1991), page 251; Wang and Herron, *J. Phys. Chem.*, 95, 525 (1991); Olshaysky et al., *J. Am. Chem. Soc.*, 112, 9438 (1990); Ushida et al., *J. Phys. Chem.*, 95, 5382 (1992), all of which are incorporated herein by reference.

Suitable nanoparticles are also commercially available from, e.g., Ted Pella, Inc. (gold), Amersham Corporation (gold) and Nanoprobes, Inc. (gold).

Presently preferred for use in detecting nucleic acids are gold nanoparticles because of their stability, ease of imaging by electron microscopy, and well-characterized modification with thiol functionalities.

The nanoparticles, the oligonucleotides, or both are functionalized in order to attach the oligonucleotides to the nanoparticles. Such methods are known in the art. For instance, oligonucleotides functionalized with alkanethiols at their 3'-termini or 5'-termini readily attach to gold nanoparticles. See Whitesides, *Proceedings of the Robert A. Welch Foundation* 39th *Conference On Chemical Research Nanophase Chemistry*, Houston, Tex., pages 109-121 (1995). See also, Mucic et al., *Chem. Commun.* 555-557 (1996), which describes a method of attaching 3' thiol DNA to flat gold surfaces; this method can be used to attach oligonucleotides to nanoparticles. The alkanethiol method can also be used to attach oligonucleotides to other metal, semiconductor, and magnetic colloids and to the other nanoparticles listed above. Other functional groups for attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, *Chemical Technology*, 4, 370-377 (1974) and Matteucci and Caruthers, *J. Am. Chem. Soc.*, 103, 3185-3191 (1981) for binding of oligonucleotides to silica and glass surfaces, and Grabar et al., *Anal. Chem.*, 67, 735-743 for binding of aminoalkylsiloxanes and for similar binding of mercaptoakylsiloxanes). Oligonucleotides terminated with a 5' thionucleoside or a 3' thionucleoside may also be used for attaching oligonucleotides to solid surfaces. The following references describe other methods that may be employed to attached oligonucleotides to nanoparticles: Nuzzo et al., *J. Am. Chem. Soc.*, 109, 2358 (1987) (disulfides on gold); Allara and Nuzzo, *Langmuir*, 1, 45 (1985) (carboxylic acids on aluminum); Allara and Tompkins, *J. Colloid Interface Sci.*, 49, 410-421 (1974) (carboxylic acids on copper); Iler, *The Chemistry Of Silica*, Chapter 6, (Wiley 1979) (carboxylic acids on silica); Timmons and Zisman, *J. Phys. Chem.*, 69, 984-990 (1965) (carboxylic acids on platinum); Soriaga and Hubbard, *J. Am. Chem. Soc.*, 104, 3937 (1982) (aromatic ring compounds on platinum); Hubbard, *Acc. Chem. Res.*, 13, 177 (1980) (sulfolanes, sulfoxides and other functionalized solvents on platinum); Hickman et al., *J. Am. Chem. Soc.*, 111, 7271 (1989) (isonitriles on platinum); Maoz and Sagiv, *Langmuir*, 3, 1045 (1987) (silanes on silica); Maoz and Sagiv, *Langmuir*, 3, 1034 (1987) (silanes on silica); Wasserman, et al., *Langmuir*, 5, 1074 (1989) (silanes on silica); Eltekova and Eltekov, *Langmuir*, 3, 951

(1987) (aromatic carboxylic acids, aldehydes, alcohols and methoxy groups on titanium dioxide and silica); Lec, et al., *J. Phys. Chem.*, 92, 2597 (1988) (rigid phosphates on metals).

Oligonucleotides functionalized with a cyclic disulfide are within the scope of this invention. The cyclic disulfides preferably have 5 or 6 atoms in their rings, including the two sulfur atoms. Suitable cyclic disulfides are available commercially or may be synthesized by known procedures. The reduced form of the cyclic disulfides can also be used.

Electrical Readers

Suitable electrical reading devices include any device for low power printed circuit board electronics capable of measuring either sequentially or in parallel a small change in conductivity, resistivity, capacitance, or impedance. The Agilent 4155C semiconductor parameter analyzer and the Agilent 4156C semiconductor parameter analyzer are examples of suitable devices. The measurements can also be carried out using inexpensive multimeters. The measurement electronics unit can also be made very small (e.g., 2 cm by 2 cm), allowing the detection in the field (e.g., doctor's office or battle field).

Methods of Use

The invention provides a nanotechnology-based low-power, rapid, inexpensive, and sensitive single-particle electrical detection device, system, and method for detection of molecular level concentrations of nucleic acid sequences, including genes, amino acid sequences, or non-biological molecules with no labeling or other chemical modification of the sample. The invention may be used in a wide variety of applications requiring sensitive nucleic acid sequence, amino acid sequence, or non-biological molecule detection, including, but not limited to, forensics, early disease detection, disease progression monitoring (such as in response to therapy and/or medicinal agents), legal matters (such as paternity and criminal proceedings), defensive biohazard detection, explosives detection, and immigration issues (such as establishing blood relationships). The biosensors of the invention are useful in further enabling "personalized medicine," where drugs are designed according to each individual's genetic make-up.

Methods of Detecting Nucleic Acids

In one aspect, the invention is directed to methods for detecting nucleic acid hybridization, comprising:
providing a device described herein;
providing a first oligonucleotide target;
wherein the capture nanoparticle comprises a first single-stranded oligonucleotide having a first nucleotide sequence complementary to a portion of the first oligonucleotide target;
wherein the oligonucleotide target hybridizes a portion of the first nucleotide sequence thereby leaving an unhybridized portion of the oligonucleotide target;
providing a plurality of first probe nanoparticles under hybridizing conditions;
wherein the first probe nanoparticles comprise at least one nanoparticle and a probe oligonucleotide complementary to the unhybridized portion of the single-stranded oligonucleotide target;
wherein the nanoparticle in the first probe nanoparticle is a metal, semiconductor, or magnetic nanoparticle;
applying a voltage drop across the electrodes; and
measuring a change in conductivity, resistivity, capacitance, or impedance across the electrodes at known locations to determine complementarity of the oligonucleotide target to the first nucleotide sequence and also the complementarity of the oligonucleotide target to the probe oligonucleotide sequence.

In certain embodiments, the measuring step measures an increase in conductivity across the electrodes at known locations to determine complementarity of the oligonucleotide target to the first nucleotide sequence and also the complementarity of the oligonucleotide target to the probe oligonucleotide sequence.

In certain embodiments, a single-stranded oligonucleotide target is prepared by heating a solution comprising double-stranded oligonucleotide target.

In certain embodiments, the methods further comprises washing to remove unhybridized components from the detecting unit.

In certain embodiments, the methods comprise:
providing a device described herein;
providing an oligonucleotide target;
wherein the oligonucleotide target hybridizes a portion of the at least one second nucleotide sequence thereby leaving an unhybridized portion of the oligonucleotide target;
providing a plurality of at least one second probe nanoparticles under hybridizing conditions;
wherein the second probe nanoparticles comprise at least one nanoparticle and a probe oligonucleotide complementary to the unhybridized portion of the single-stranded oligonucleotide target;
wherein the nanoparticle in the second probe nanoparticle is a metal, semiconductor, or magnetic nanoparticle;
wherein the second probe nanoparticles are the same or different from the first probe nanoparticles;
wherein the second probe nanoparticles are the same or different from the other second probe nanoparticles;
wherein the measuring step is carried out in parallel or sequentially for the first detecting unit and the plurality of the additional detecting units.

It would be desirable to detect the oligonucleotide target in as short time as possible, which requires enhancing the hybridization kinetics. There have been a number of studies toward efficient DNA hybridization. Using microfluidic microarrays and re-circulation mixing (called shuttle hybridization), Cheng and co-workers demonstrated hybridization time as short as ~8 minutes for target concentration of 19 aM with 1 µl sample volume (Wei, C. W., Cheng, J. Y., Huang, C. T., Yen, M. H. & Young, T. H. Using a microfluidic device for 1 µl DNA microarray hybridization in 500 s. *Nucleic Acids Research* 33, e78 (2005)). Similarly short hybridization times, ranging from 5 to 60 minutes, have been reported by others as well for target concentrations ranging from 10 pM to 20 fM, also for microfluidic microarray setups. (Benn, J. A., Hu, J., Hogan, B. J., Fry, R. C., Samson, L. D. and Thorsen, T. Comparative modeling and analysis of microfluidic and conventional DNA microarrays. *Analytical Biochemistry* 348, 284-293 (2006); Lee, H. J., Goodrich, T. T. & Corn, R. M. SPR imaging measurements of 1-D and 2-D DNA microarrays created from microfluidic channels on gold thin films. *Analytical Chemistry* 73, 5525-5531 (2001)). Considering that the device of the invention needs a much smaller number of T-oligo molecules to produce a signal (even one P-NP/C-NP conjugate that bridges source and drain electrodes will produce a signal), the hybridization time of the devices of the invention can be made short (<1 hour), if hybridization enhancement techniques including microfluidics/forced convection and control of film thickness of the solution are used.

In certain embodiments, the methods further comprise: washing to remove unhybridized components from the detecting unit.

In certain embodiments, the methods further comprise: heating the device to remove the hybridized targets and the hybridized probe nanoparticles from the probe to permit recycling of the detecting unit.

In certain embodiments, the methods further comprise: heating a solution comprising double stranded oligonucleotide target to form the solution comprising single-stranded oligonucleotide target.

In certain embodiments, the methods further comprise: forming a temperature gradient to focus the single stranded oligonucleotide target at the detecting unit.

In certain embodiments, the methods further comprise: applying an electric field to direct the oligonucleotide target to the capture unit to reduce the hybridization time.

The methods of the invention may be used to quantify the level of oligonucleotides or polypeptides. For example, the change in conductance (or other electrical characteristic) between the source and drain electrodes is direct function of the number of single-particle bridges that electrically connect the source and drain electrodes. The number of single-particle bridges formed is a direct function of the number of complementary oligonucleotides that have hybridized or the number of polypeptides that have bounded to the antibodies. Thus, the change of conductivity (or other electrical characteristic) can be directly correlated to the quantity of complementary oligonucleotides or polypeptides present in the sample.

In certain embodiments, the voltage drop is applied as direct current. In other embodiments, the voltage drop is applied as alternating current and the alternating current impedance measured.

In certain embodiments, the measuring step measures an increase in conductivity across the electrodes at known locations to determine complementarity of the oligonucleotide target to the first oligonucleotide and also complementarity of the oligonucleotide target to the probe oligonucleotide.

In certain embodiments, a single-stranded oligonucleotide target is prepared by heating a solution comprising double-stranded oligonucleotide target.

In one embodiment, the oligonucleotide target is a DNA or RNA aptamer.

In certain embodiments, the invention is directed to methods for detecting nucleic acid hybridization, comprising the optional step to enhance detection of the nucleic acid of reversibly exchanging an imino proton in each base pair of the probe, target or capture oligonucleotides with a metal ion selected from the group consisting of gold ion, silver ion, platinum ion, and copper ion. The reversible exchanging of an imino proton in each base pair may be carried out as described in A. Rakitin, Aich, P., Papadopoulos, C., Kobzar, Yu., Vedeneev, A. S., Lee, J. S., J. M. Xu, *Phys. Rev. Lett.,* 86(16), 3670-3673, (2001), which is incorporated herein by reference.

In certain embodiments, the invention is directed to methods for detecting nucleic acid hybridization, comprising the optional step to enhance detection of the nucleic acid of vectorially depositing silver on the double stranded nucleic acid sequence. In certain embodiments of this method, the vectorially depositing step comprises: ion exchanging silver ions on the double stranded nucleic acid sequence; reducing the silver ions; and developing silver aggregates on the double stranded nucleic acid sequence; as described in E. Braun, Y. Eichen, U. Sivan, and G. Ben-Yoseph, *Nature,* 391(6669), 775-778, (1998), incorporated herein by reference.

In certain embodiments, the invention is directed to methods for detecting nucleic acid hybridization, comprising the optional step to enhance detection of the nucleic acid of providing a solution comprising nanoparticle polypeptide conjugates; wherein the nanoparticle polypeptide conjugates comprise at least one nanoparticle and a polypeptide (for example comprising at least one residue of cysteine) that binds to the double stranded oligonucleotide-stem complex.

In some embodiments, the single-particle bridge assay is used to detect nucleic acids for predicting or diagnosing a cancer. In some embodiments, the cancer can be selected from breast cancer, lung cancer, prostate cancer, liver cancer, ovarian cancer, or other human or animal cancers.

In some embodiments, the single-particle bridge assay is used to detect nucleic acids for detection of an infectious disease or a biological weapon. In some embodiments, the infectious disease is selected from Zika virus, Ebola virus, anthrax, polio, HIV, hepatitis A, hepatitis B, hepatitis C, or additional human or animal pathogens of interest.

In some embodiments, the single-particle bridge assay is used to detect nucleic acids for detection of pathogens in food products or agriculture. In some embodiments, the pathogen to be detected is selected from *E. coli, Salmonella, Norovirus, Brucella, Mycobacterium, Toxoplasma gondii*, or additional pathogens of interest for food safety and agricultural purposes.

Methods of Detecting Polypeptides

In other embodiments, the invention is directed to methods of detecting a polypeptide (for example, a protein, antigen, antibody, enzyme, or protein-antibody interaction), comprising:

providing a device described above, wherein the capture nanoparticle is comprised of a plurality of first antibodies attached to the capture nanoparticle;

providing a polypeptide target;

wherein the first antibodies have an affinity to a portion of the polypeptide target;

providing a plurality of first probe nanoparticles under hybridizing conditions;

wherein the first probe nanoparticles comprise at least one nanoparticle and a second antibody capable of binding an unbound portion of the polypeptide target;

wherein the probe nanoparticle is a metal, semiconductor, or magnetic nanoparticle; applying a voltage drop across the electrodes; and measuring a change in conductivity, resistivity, capacitance, or impedance across the electrodes at known locations to determine binding of the polypeptide target to the first antibodies and to determine binding of the polypeptide target to the second antibodies.

In certain embodiments, the methods further comprise: washing to remove unbound components from the detecting unit.

In one embodiment, the polypeptide target is a peptide aptamer.

The clinical setting requires performing the same test on many patient samples. The automated methods of this invention lend themselves to these uses when the test is one appropriately performed on a biological chip. For example, a DNA array can determine the particular strain of a pathogenic organism based on characteristic DNA sequences of the strain. The advanced techniques based on these assays now can be introduced into the clinic. Fluid samples from several patients are introduced into the test wells of a biological chip plate and the assays are performed concurrently.

In some embodiments, it may be desirable to perform multiple tests on multiple patient samples concurrently. According to such embodiments, rows (or columns) of the microtiter plate will contain probe arrays for diagnosis of a particular disease or trait. For example, one row might contain probe arrays designed for a particular cancer, while other rows contain probe arrays for another cancer. Patient samples are then introduced into respective columns (or rows) of the microtiter plate. For example, one column may be used to introduce samples from patient "one," another column for patient "two" etc. Accordingly, multiple diagnostic tests may be performed on multiple patients in parallel. In still further embodiments, multiple patient samples are introduced into a single well. In a particular well indicator the presence of a genetic disease or other characteristic, each patient sample is then individually processed to identify which patient exhibits that disease or trait. For relatively rarely occurring characteristics, further order-of-magnitude efficiency may be obtained according to this embodiment.

Particular assays that will find use in automation include those designed specifically to detect or identify particular variants of a pathogenic organism, such as HIV. Assays to detect or identify a human or animal gene are also contemplated. In one embodiment, the assay is the detection of a human gene variant that indicates existence of or predisposition to a genetic disease, either from acquired or inherited mutations in an individual DNA. These include genetic diseases such as cystic fibrosis, diabetes, and muscular dystrophy, as well as diseases such as cancer (the P53 gene is relevant to some cancers), as disclosed in U.S. Pat. No. 5,837,832.

In some embodiments, the single-particle bridge assay is used to detect polypeptides for predicting or diagnosing a cancer. In some embodiments, the cancer can be selected from breast cancer, lung cancer, prostate cancer, liver cancer, ovarian cancer, or other human or animal cancers.

In some embodiments, the single-particle bridge assay is used to detect polypeptides for detection of an infectious disease or a biological weapon. In some embodiments, the infectious disease is selected from Zika virus, Ebola virus, anthrax, polio, HIV, hepatitis A, hepatitis B, hepatitis C, or additional human or animal pathogens of interest.

In some embodiments, the single-particle bridge assay is used to detect polypeptides for detection of pathogens in food products or agriculture. In some embodiments, the pathogen to be detected is selected from *E. coli, Salmonella, Norovirus, Brucella, Mycobacterium, Toxoplasma gondii*, or additional pathogens of interest for food safety and agricultural purposes.

Methods of Detecting Non-Biological Molecules

In addition to detection of biological molecules such as nucleic acids and polypeptides, the single-particle bridge assay (SPBA) can be used for the single-molecule-level detection of non-biological molecules. Examples of non-biological molecules include, for example, explosives (for example, dinitrotoluene (DNT) and 2,4,6-trinitrotoluene (TNT)), aroma (scent) molecules, etc. Such molecular sensors can be made with the following: (1) The capture molecule (on the capture nanoparticle) specifically binds to the target molecule. (2) The probe molecule (on the probe nanoparticle) specifically binds to another portion of the target molecule.

In one embodiment, disclosed herein is a method of detecting a non-biological molecule, comprising:

providing a device as described herein;

wherein the capture nanoparticle is comprised of a plurality of first capture molecules attached to the nanoparticle; and wherein the capture nanoparticle is a metal, semiconductor, or magnetic nanoparticle;

providing a target molecule;

wherein the first capture molecules have an affinity to a portion of the target molecule;

providing a plurality of first probe nanoparticles under hybridizing conditions;

wherein the first probe nanoparticles comprise at least one nanoparticle and a probe molecule capable of binding an unbound portion of the target molecule;

wherein the probe nanoparticle is a metal, semiconductor, or magnetic nanoparticle;

applying a voltage drop across the electrodes; and measuring a change in conductivity, resistivity, capacitance, or impedance across the electrodes at known locations to determine binding of the target molecule to the first capture molecule and to determine binding of the target molecule to the probe molecule.

It will be apparent to those skilled in the art that various modifications and variations can be made in the present invention and specific examples provided herein without departing from the spirit or scope of the invention. Thus, it is intended that the present invention cover the modifications and variations of this invention that come within the scope of any claims and their equivalents.

EXAMPLES

The following examples are set forth below to illustrate the devices, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1

Single-Particle Bridge Assay for Detection of Nucleic Acids

Figure 1B:
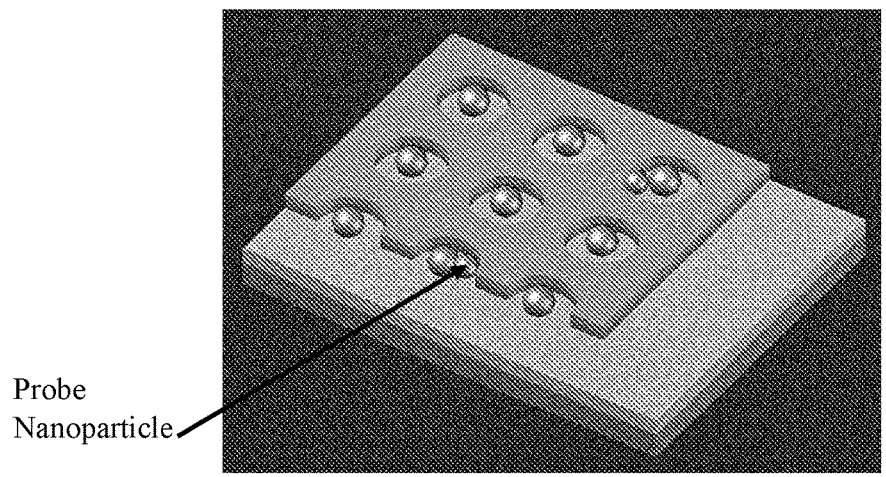
FIG. 1B shows the single-particle bridge assay schematic after addition of the oligonucleotide target sequence and the probe nanoparticles (P-NPs). The capture nanoparticle (C-NP) is a nanoparticle on which capture oligonucleotide (C-oligo) molecules are attached. Nanoparticle-bridge conjugates are formed that electrically bridge the drain electrode and source electrode (oligonucleotides on the nanoparticles are not shown in FIGS. 1A and 1B for image clarity).
Figure 1C:
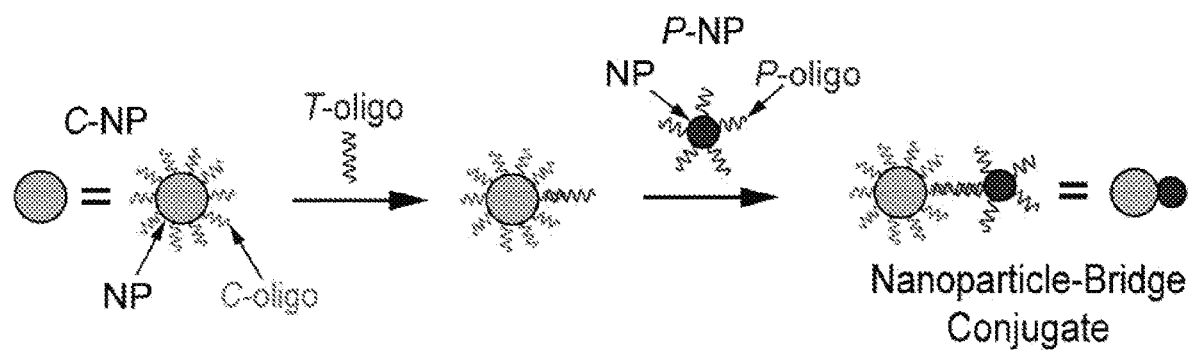
FIG. 1C shows a schematic of the formation of the single nanoparticle bridge conjugate. The probe nanoparticle (P-NP) is a nanoparticle on which probe oligonucleotide (P-oligo) molecules are attached. The capture oligonucleotide (C-oligo) is complementary to one portion of the oligonucleotide target (T-oligo) and the probe oligonucleotide (P-oligo) is complementary to the remaining portion of the T-oligo. Formation of the single-particle bridge can be electrically detected.
Figure 1D:
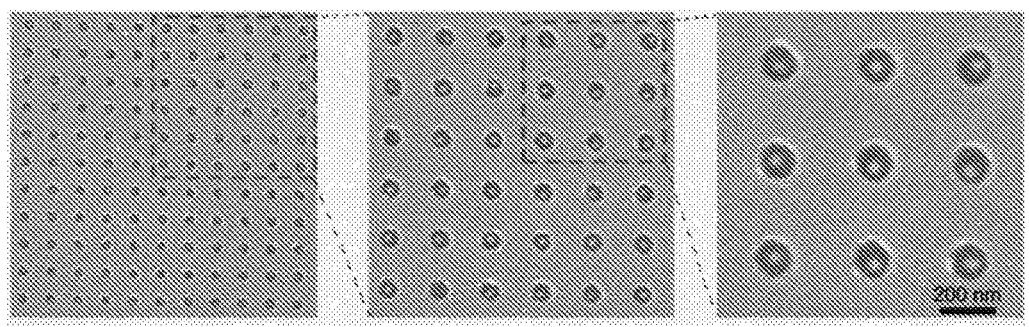
FIG. 1D shows a scanning electron micrograph (SEM) image of the single-particle bridge assay device prior to addition of the oligonucleotide target and probe nanoparticles.

The single-particle bridge assay (SPBA) is illustrated in FIGS. 1A-1E. First, capture nanoparticles (C-NPs) on which capture oligonucleotides (C-oligo) are immobilized are placed at the center positions of the circular holes of the drain electrode and the circular holes of the dielectric layer (FIG. 1A). Here, the assay unit is fabricated on a Si wafer (substrate) with three different material layers (Cr (source electrode), $SiO_2$ (dielectric layer), and Au (drain electrode) layers) arranged in a configuration in FIG. 1A, in which the insulating $SiO_2$ layer (dielectric layer) electrically disconnects the top Au layer (drain electrode) from the metal Cr layer underneath (source electrode). The capture nanoparticles (C-NPs) are in contact with the metal Cr layer (source electrode). A portion of a single-particle bridge biosensor device is shown in FIG. 1D. FIG. 1D provides a scanning electron micrograph of one example illustrating an array of circular holes (where the circular holes extend through the drain electrode and dielectric layer, but do not through the source electrode). A single capture nanoparticle can be seen centered in the middle of each circular hole.

Figure 2:
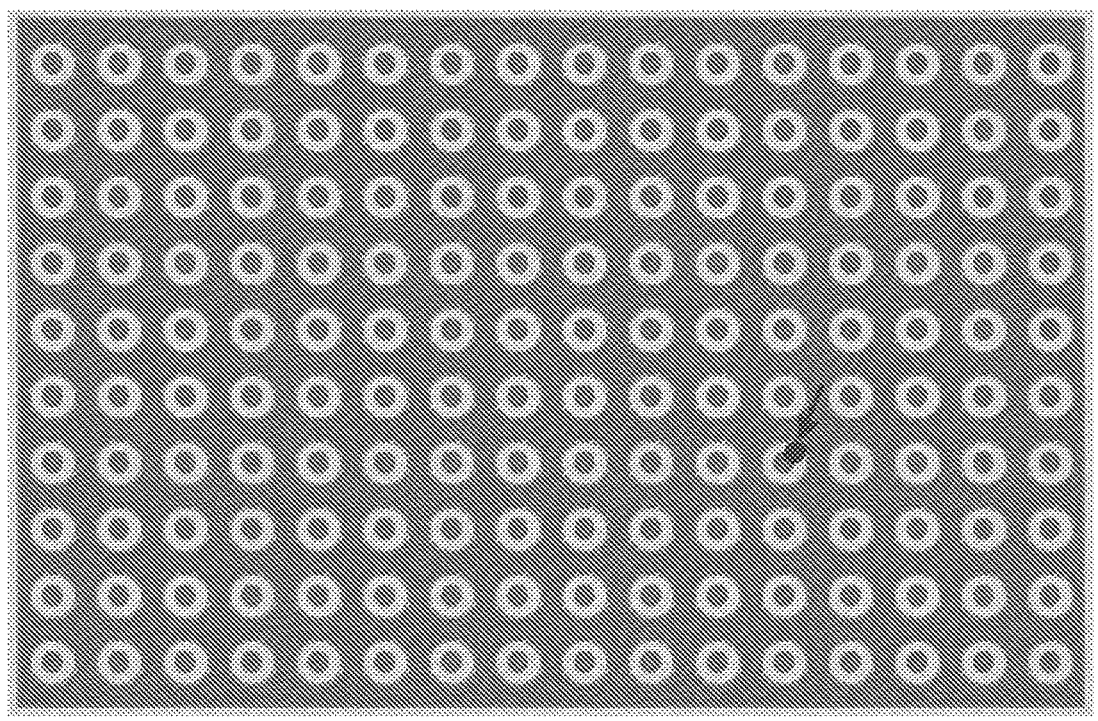
FIG. 2 shows an illustration of the detection of a single target molecule using the single-particle bridge assay (SPBA). The arrow points to a single probe nanoparticle binding to a capture nanoparticle, forming a single-particle bridge, resulting in the production of an electrical current.

In the next step, a solution containing oligonucleotide targets (T-oligo) is introduced, followed by an introduction of P-NPs, where the presence of the T-oligo molecules leads to the formation of nanoparticle-bridge conjugates (FIG. 1B; arrow in FIG. 2), which electrically bridge the top Au layer and the metal Cr layer (FIG. 1B). The formation of the nanoparticle-bridge conjugates is further illustrated in FIG. 1C. Briefly, a T-oligo is captured by a C-NP through hybridization between the T-oligo and the C-oligo. When probe nanoparticles (P-NPs; abundant) on which probe oligonucleotides (P-oligo) are immobilized are introduced, a P-NP is captured by the C-NP through hybridization between the P-oligo and the T-oligo, producing a nanoparticle-bridge conjugate (FIG. 1C). The final nanoparticle-bridge conjugate of the single-particle bridge assay (SPBA) (See FIG. 1B, 1C, and FIG. 2) is electrically detected by applying a voltage bias between the Cr layer (source electrode) and the Au layer (drain electrode) and measuring the current.

Figure 1E:
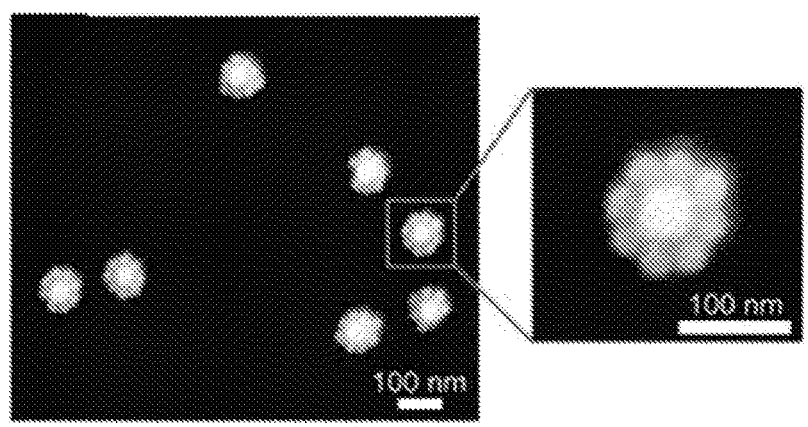
FIG. 1E shows a scanning electron micrograph (SEM) image of the formation of nanoparticle-bridge conjugates after addition of the oligonucleotide target and probe nanoparticles on a blanket $SiO_2$ substrate.
Figure 7A:
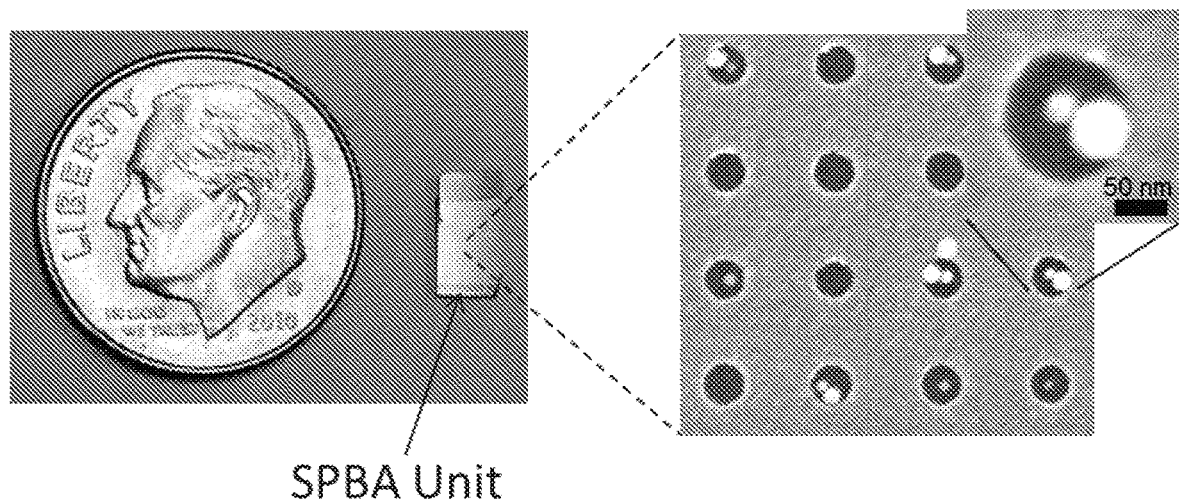
FIG. 7A shows a picture (left panel) and a scanning electron micrograph (SEM) image (right panel) of the single-particle bridge assay device after addition of the anthrax oligonucleotide target and anthrax probe nanoparticle. The left panel shows the SPBA unit juxtaposed with a dime to provide a sense of the relative size of the SPBA unit. As seen in the right panel, the probe nanoparticle is shown bridging form the capture nanoparticle to the drain electrode.
Figure 7B:
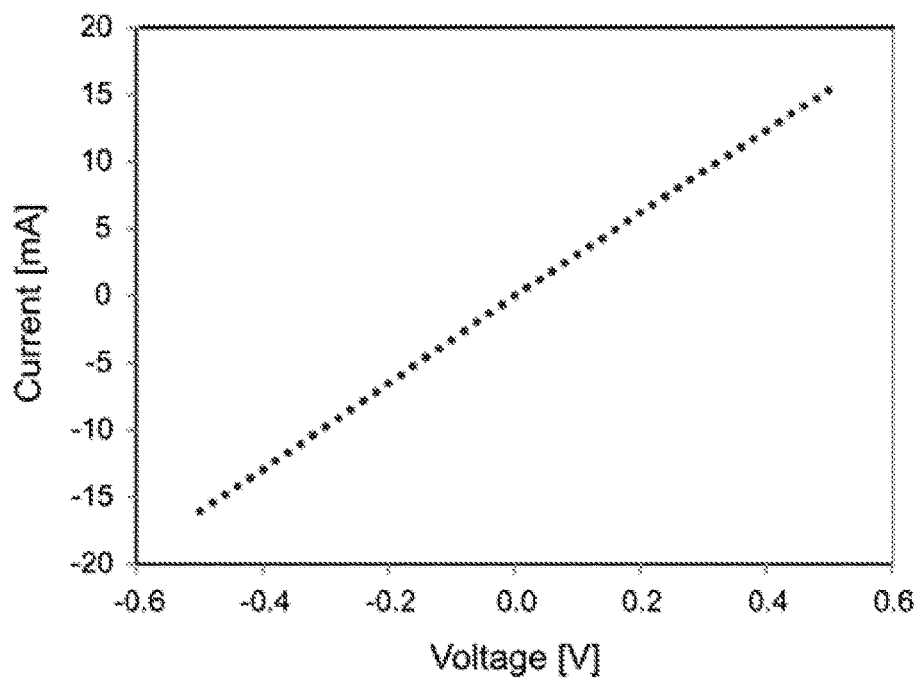
FIG. 7B shows the measured current (mA) vs. voltage (V) characteristics for detection of the anthrax DNA.

In one example, the single-particle bridge assay (SPBA) is used to detect anthrax DNA. For the detection of anthrax DNA, the C-oligo, T-oligo and P-oligo have the following sequences: C-oligo: 5'-$T_{20}$ATCCTTATCAATATTTAA-3' (SEQ ID NO:1); T-oligo (anthrax DNA): 3'-TAG-GAATAGTTATAAATTGTTATTAGGGAG-5' (SEQ ID NO:2); P-oligo: 5'-CAATAATCCCTCT2o-3' (SEQ ID NO:3). FIG. 1D shows SEM micrographs in which the C-NPs that are coated with the anthrax C-oligos are placed on the center positions of the circular holes. FIG. 1E shows a scanning electron micrograph (SEM) in which anthrax C-oligo, anthrax T-oligo, and anthrax P-oligo (having the sequences above) are used to demonstrate the formation of nanoparticle-bridge conjugates. FIG. 7A a picture of a device relative to a dime and shows a scanning electron micrograph (SEM) of the SPBA device after the single-particle bridge assay for anthrax DNA is completed. FIG. 7B shows measured electrical characteristics of an SPBA for the anthrax DNA in which the linear correlation of the current (mA) vs. voltage (V) for detection of the anthrax DNA is demonstrated.

Figure 11:
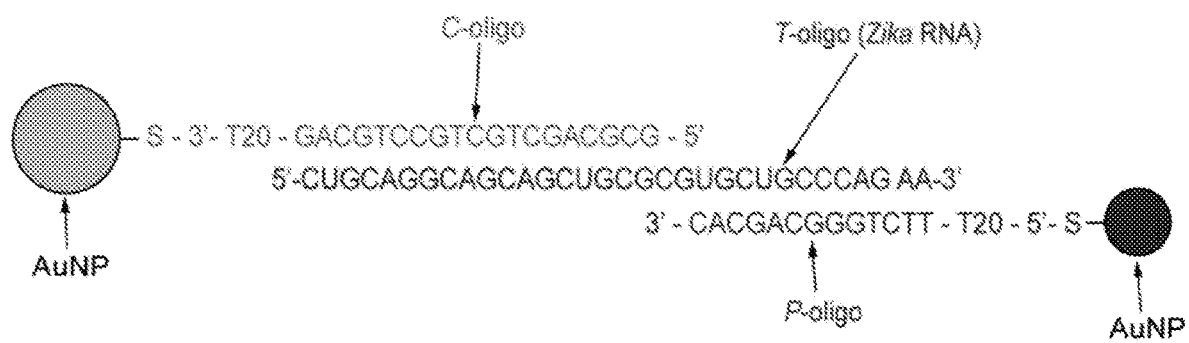
FIG. 11 shows a schematic for a method of detecting Zika virus. A capture oligonucleotide (C-oligo; first single-stranded oligonucleotide) is attached to the capture nanoparticle. A probe oligonucleotide (P-oligo) to Zika virus is attached to the probe nanoparticle. The presence of the target Zika virus RNA (T-oligo) hybridizes to the capture nanoparticle and the probe nanoparticle to form a nanoparticle-bridge conjugate.

In one example, the single-particle bridge assay (SPBA) is used to detect Zika virus RNA. For the detection of Zika virus RNA, the C-oligo, T-oligo and P-oligo have the following sequences: C-oligo: 3'-$T_{20}$-GACGTCCGT1GTCGACGCG5' (SEQ ID NO:4); T-oligo (Zika virus RNA): 5'-CUGCAGGCAGCAGCUGCGCGUGCUGCCCAGAA-3' (SEQ ID NO:5); P-oligo: 3' CACGACGGGTCTT-$T_{20}$-5' (SEQ ID NO:6). FIG. 11 shows a schematic for a method of detecting Zika virus. A capture oligo is attached to the capture nanoparticle. A probe oligo to Zika virus is attached to the probe nanoparticle. The presence of the target Zika virus RNA hybridizes to the capture nanoparticle and the probe nanoparticle to form a nanoparticle-bridge conjugate.

There are a number of benefits to the single-particle bridge assay (SPBA) in comparison to previous devices and methods. First, a capture of even a single T-oligo molecule by a C-NP can form a nanoparticle-bridge conjugate and produce a signal. The SPBA unit in FIG. 1A contains numerous C-NPs to readily capture T-oligo molecules even in a very low concentration. Here, even a capture of a single T-oligo molecule (See FIG. 2) by one of the millions or billions of C-NPs leads to a formation of a nanoparticle-bridge conjugate as the P-NPs introduced are abundant and therefore readily captured by the single T-oligo. Second, no signal amplification is needed. Even a formation of one single-particle bridge (see FIG. 2) provides an electrical path between the drain electrode and the source electrode and therefore a voltage bias between the electrodes readily produces a detectable current. Because of the ability of the SPBA assay to detect such low levels of nucleic acid, it is not necessary to add an additional amplification step (e.g., PCR) in order to detect the target sequence. Third, T-oligo concentration can be quantitatively detected over a wide range of T-oligo concentrations. This is because the capture probability of the T-oligos by the C-NPs is proportional to the T-oligo concentration and therefore the resulting number of single-particle bridges (the number of P-NPs) is proportional to the T-oligo concentration (See FIG. 5).

An additional benefit of the SPBA assay comes from the direct electrical currents that are measured for the assay output without transducers. The optical or radioactive outputs of the usual oligonucleotide assays require sophisticated instrumentations including optics, laser sources, photo detectors, radioactive detectors, transducers, etc. Considering this, the direct electrical output of the SPBA has many practical advantages, such as compactness, portability, low cost, and facile integrations with other systems.

Figure 9A:
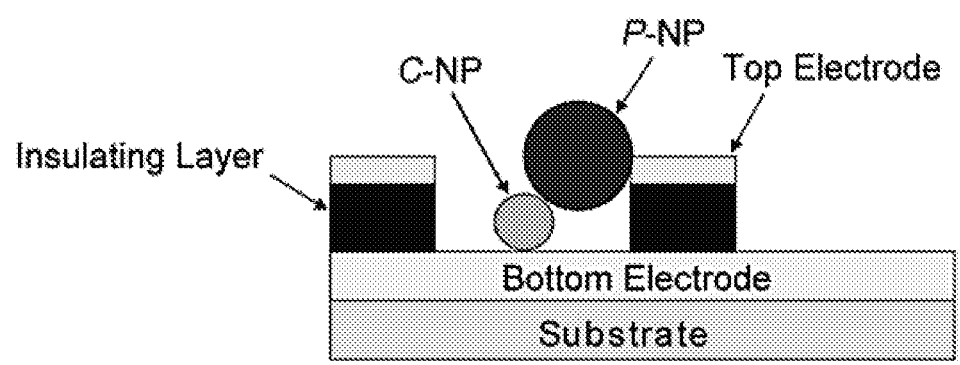
FIG. 9A shows a schematic of the single-particle bridge assay (SPBA) device set up after the detection of a target molecule using a capture nanoparticle that is smaller than the probe nanoparticle. The capture nanoparticles (C-NPs) are electrostatically funneled into the center locations of the circular holes of the drain electrode and dielectric layer. The drain electrode (top electrode) is electrically separated from the source electrode (bottom electrode) by a dielectric layer (an insulating layer). The capture nanoparticle is in contact with the source electrode. In this SPBA device, the capture nanoparticle is smaller than the probe nanoparticle. In addition, the thickness of the insulating layer is larger than the diameter of the C-NP. The substrate is Si, etc. The bottom electrode is Cr, Si, or other metals and semiconductors. The insulating layer is $SiO_2$, $Si_3N_4$, etc.
Figure 9B:
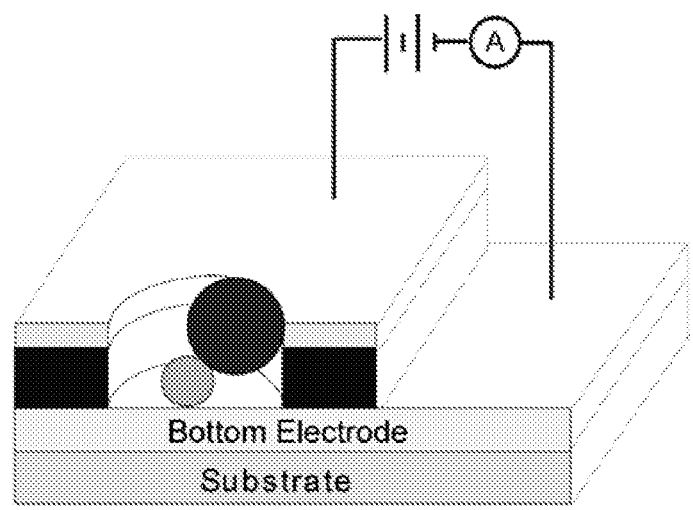
FIG. 9B shows a 3-D schematic of the single-particle bridge assay (SPBA) device set up after the detection of a target molecule using a capture nanoparticle that is smaller than the probe nanoparticle.
Figure 10A:
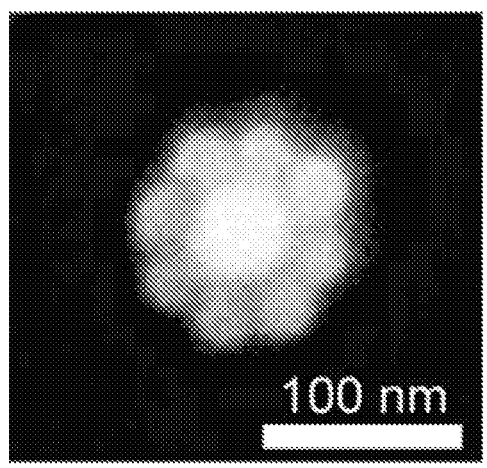
FIG. 10A shows a scanning electron micrograph (SEM) image of the formation of nanoparticle-bridge conjugates where the capture nanoparticles are larger than the probe nanoparticles.
Figure 10B:
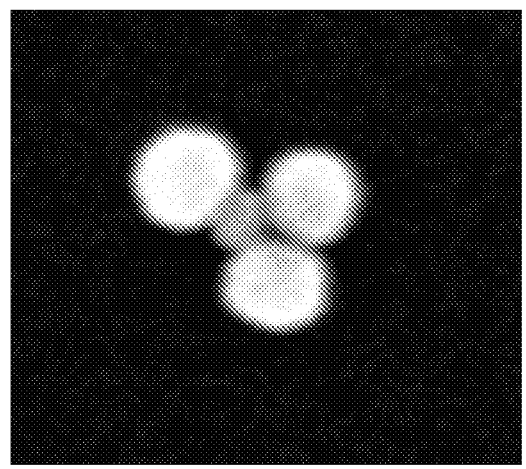
FIG. 10B shows a scanning electron micrograph (SEM) image of the formation of nanoparticle-bridge conjugates where the capture nanoparticles are smaller than the probe nanoparticles.

The single-particle bridge assay (SPBA) is also illustrated in FIGS. 9A-9B using a probe nanoparticle that is larger than the capture nanoparticle. First, capture nanoparticles (C-NP) on which capture oligonucleotides are immobilized are placed at the center positions of the circular holes of the drain electrode (top electrode) and the circular holes of the dielectric layer (insulating layer) (FIG. 9A: cross-sectional view; FIG. 9B: 3-D view). Here, the assay unit is fabricated on a substrate (e.g., Si wafer) with three different material layers (source (or bottom) electrode (e.g., Cr), dielectric (insulating) layer (e.g., $SiO_2$), and drain (or top) electrode (e.g., Au) layers) arranged in a configuration in FIG. 9A, in which the insulating layer (dielectric layer; e.g., $SiO_2$) electrically disconnects the top electrode (drain electrode) from the bottom electrode underneath (source electrode). The capture nanoparticles (C-AuNPs) are in contact with the bottom electrode (source electrode). The probe nanoparticle can be larger than the capture nanoparticle and can form the single-particle bridge. FIGS. 10A and 10B show a scanning electron micrograph comparing particles where the capture particle is larger than the probe nanoparticle (FIG. 10A) or where the probe nanoparticle is larger than the capture nanoparticle (FIG. 10B).

Figure 8:
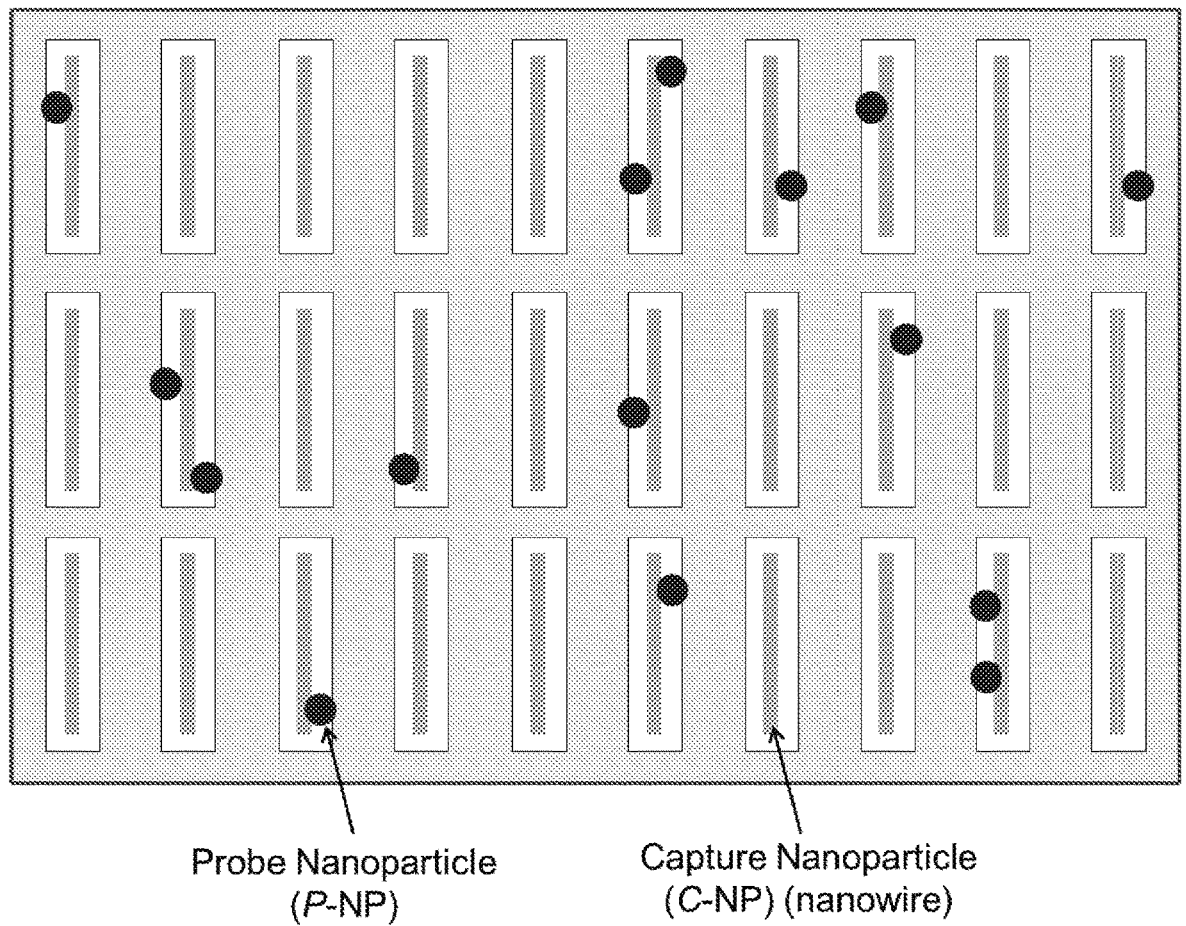
FIG. 8 shows a schematic of the single-particle bridge assay (SPBA) device set up after the detection of the oligonucleotide target, using a nanowire, instead of a nanoparticle. Instead of capture nanoparticles located in the center of circular holes in the drain electrode and dielectric layer, a capture nanowire may be used in place of the capture nanoparticle. Instead of circular holes, the device comprises an array of rectangular holes in the drain electrode and dielectric layers. The rectangular holes have a nanowire centered in the hole, such that a nanoparticle can bridge the distance between the capture nanowire and the drain electrode layer.

In some examples, the nanoparticle of the device is not spherical, but is instead shaped like a wire (nanowire). FIG. 8 shows a schematic of the single-particle bridge assay (SPBA) device set up after the detection of the oligonucleotide target. Instead of capture nanoparticles located in the center of circular holes in the drain electrode and dielectric layer, a capture nanowire may be used in place of a spherical capture nanoparticle. Instead of circular holes, the device comprises an array of rectangular holes in the drain electrode and dielectric layers. The rectangular holes comprise a capture nanowire centered in the hole, such that a probe nanoparticle (P-NP) can bridge the distance between the capture nanowire and the drain electrode layer.

Example 2

Single-Particle Bridge Assay for Detection of Polypeptides

As protein molecules cannot be directly copied and amplified, low-concentrations of proteins are normally detected only indirectly, for example, by using the PCR amplification of the nucleic acid (immuno-PCR) or other amplification methods involving barcode DNA, silver or gold enhancement, quantum dot reporter amplification and the rolling-circle amplification (immune-RCA). Considering these indirect protein detections are complex and involve many steps, the single-particle bridge assay (SPBA) can have broad application in disease diagnostics, immunoassays, and biomedical research in general.

Figure 3A:
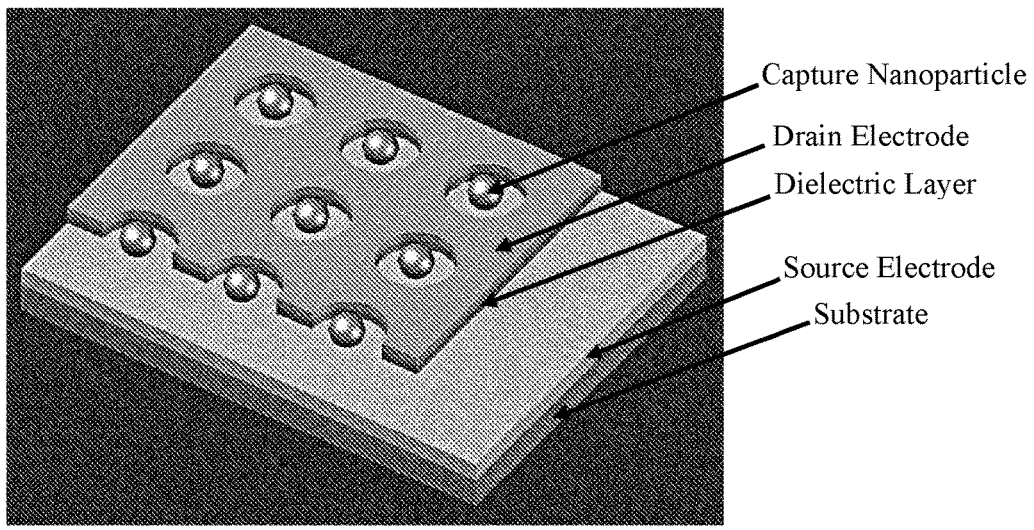
FIG. 3A shows a schematic of the single-particle bridge assay (SPBA) device for the detection of protein antigens, prior to the addition of the probe nanoparticle and the detection of the target antigen. The capture nanoparticles (C-NPs) are electrostatically funneled into the center locations of the circular holes of the drain electrode and dielectric layer. The drain electrode is electrically separated from the source electrode by a dielectric layer. The capture nanoparticle is in contact with the source electrode.
Figure 3B:
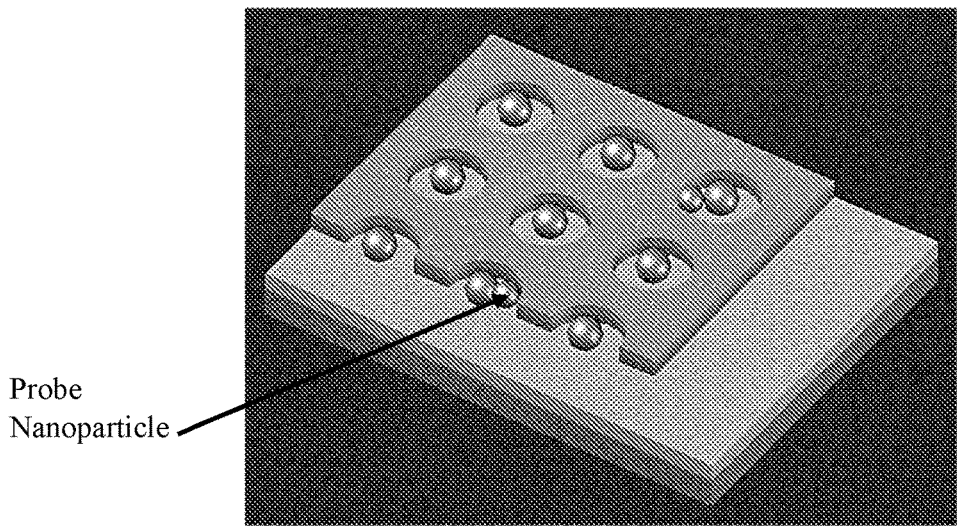
FIG. 3B shows the single-particle bridge assay schematic after addition of the target antigen and the probe nanoparticle (P-NP) containing a probe antibody. The capture nanoparticle (C-NP) is a nanoparticle on which capture antibody (C-Ab) molecules are attached. Nanoparticle-bridge conjugates are formed that electrically bridge the drain electrode and source electrode (antibodies on the nanoparticles are not shown in FIGS. 3A and 3B for image clarity).
Figure 3C:
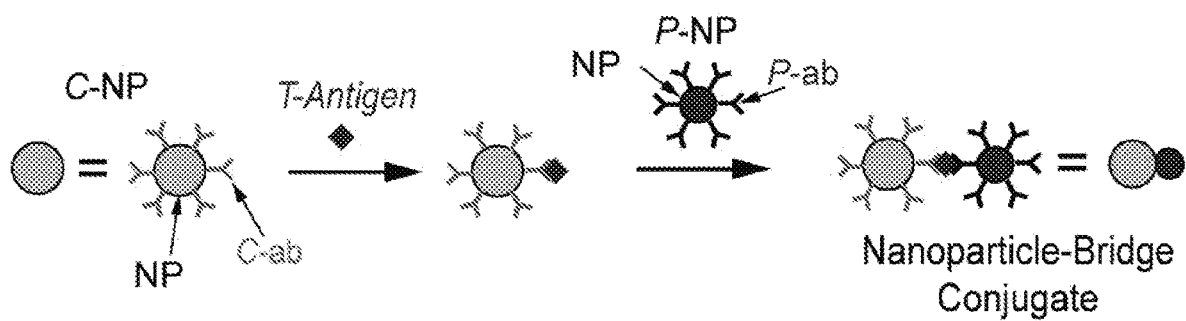
FIG. 3C shows a schematic of the formation of the single nanoparticle bridge conjugate for the detection of the target antigen. The probe nanoparticle (P-NP) is a nanoparticle on which probe antibody (P-Ab) molecules are attached. C-Ab has affinity to a portion of the target antigen and P-Ab has affinity to a remaining portion of the target antigen. Formation of the single-particle bridge can be electrically detected.

The use of the single-particle bridge assay (SPBA) for the detection of antigens is illustrated in FIGS. 3A-3C. First, capture nanoparticles (C-NPs) on which capture proteins (antibody: C-ab) are immobilized are placed at the center positions of the circular holes of the drain electrode and the circular holes of the dielectric layer (FIG. 3A). Here, the assay unit is fabricated on a substrate (e.g., Si wafer) with three different material layers (source electrode (e.g., Cr), dielectric layer (e.g., $SiO_2$), and drain electrode (e.g., Au)) arranged in a configuration in FIG. 3A, in which the insulating layer (dielectric layer) electrically disconnects the drain electrode from the source electrode. The capture nanoparticles (C-NPs) are in contact with the source electrode (e.g., metal Cr layer).

In the next step, a solution containing target proteins (antigen: T-antigen) and probe nanoparticles (P-NPs: nanoparticles with a second antibody (P-ab) attached) is introduced and the presence of the T-antigen molecules leads to the formation of nanoparticle-bridge conjugates, which electrically bridge the top drain electrode (e.g., Au layer) and the bottom source electrode (e.g., metal Cr layer) (See FIG. 3B).

The formation of the nanoparticle-bridge conjugates is further illustrated in FIG. 3C. Briefly, a T-antigen is captured by a C-NP through binding between the T-antigen and the capture proteins (antibody: C-ab). When probe nanoparticles (P-NPs; abundant) on which probe proteins (a second antibody: P-ab) are immobilized are introduced, a P-NP is captured by the C-NP through binding between the P-ab and the T-antigen, producing a nanoparticle-bridge conjugate (FIG. 3C). The final nanoparticle-bridge conjugate of the single-particle bridge assay (SPBA) (See FIGS. 3B and 3C) is electrically detected by applying a voltage bias between the source electrode (e.g., Cr layer) and the drain electrode (e.g., Au layer) and measuring the current.

Example 3

Procedure for the Single-Particle Bridge Assay (SPBA)

Figure 4:
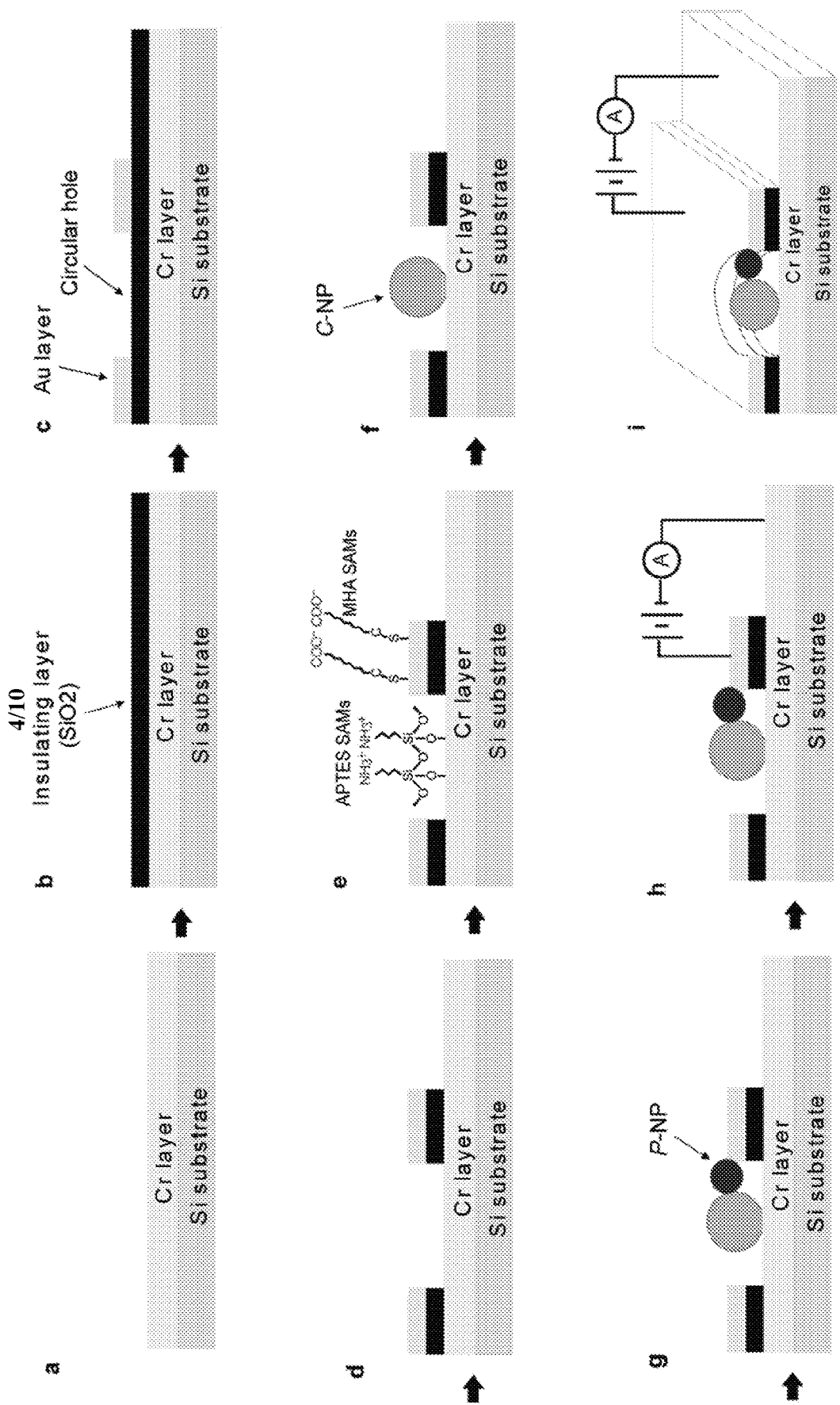
FIG. 4 shows a schematic for the experimental procedure for the preparation of the single-particle bridge assay device. Panel (a) shows a chromium (Cr) layer (source electrode) is placed on a silicon (Si) substrate. Panel (b) shows the insulating layer ($SiO_2$) is placed on the Cr layer. Panel (c) shows the placement of a gold layer (drain electrode) comprising circular holes on the insulating layer (dielectric layer). Panel (d) shows the formation of circular holes in the insulating layer (dielectric layer) by removal of the insulating layer in the circular holes (aligning the holes in the dielectric layer with those circular holes in the gold layer (drain electrode). Panel (e) shows the formation of positively- and negatively-charged self-assembled monolayers (SAMs) on the Cr and Au surfaces, respectively. This is done using SAMs of 3-aminopropyltriethoxysilane (APTES: $(C_2H_5O)_3$—Si—$(CH_2)_3$—$NH_2$; positively charged with $NH_3^+$ termination) and 16-mercaptohexadecanoic acid (MHA: HS-$(CH_2)_{15}$—COOH; negatively charged with $COO^-$ termination) for Cr and Au surfaces, respectively. Panel (f) shows the addition of the capture nanoparticle (C-NP) which is guided to the center of each circular hole via electrostatic funneling and self-limiting single-particle placement mechanism. Panel (g) shows the addition of the oligonucleotide target (not visualized in the schematic) and the probe nanoparticle (P-NP), which produces a nanoparticle-bridge conjugate, where the P-NP provides a bridge between the Au layer (drain electrode) and the C-NP in contact with the Cr layer (source electrode). Panel (h) shows the electrical detection of the nanoparticle-bridge conjugate by applying a voltage bias across the Au (drain) and Cr (source) electrodes, and measuring the current. Panel (i) shows a three-dimensional view of panel (h). The materials illustrated in this figure are to show an example; however, other materials that serve for the same purposes can be used for the SPBA.

The procedure of the single-particle bridge assay (SPBA) is schematically displayed in FIG. 4. (a) On a piece of silicon (Si) (substrate) wafer, a metal chromium (Cr) layer (source electrode) is deposited using electron-beam evaporation. (b) On the Cr layer, an insulating layer (dielectric layer) of $SiO_2$ is deposited using plasma-enhanced chemical vapor deposition (PECVD). (c) On the PECVD $SiO_2$ layer, a Au layer (drain electrode) having circular holes is formed using electron-beam lithography, Au deposition, and lift-off (only one circular hole is shown schematically; the actual assay unit contains numerous circular holes). (d) The PECVD $SiO_2$ layer inside the circular holes is removed by etching with a 2% HF solution, exposing the metal Cr inside the circular holes. (e) Positively- and negatively-charged self-assembled monolayers (SAMs) are then formed on the Cr and Au surfaces, respectively. This is done using SAMs of 3-aminopropyltriethoxysilane (APTES: $(C_2H_5O)_3$—Si—$(CH_2)_3$—$NH_2$; positively charged with $NH_3^+$ termination) and 16-mercaptohexadecanoic acid (MHA: HS-$(CH_2)_{15}$—COOH; negatively charged with $COO^-$ termination) for Cr and Au surfaces, respectively. (f) When a solution containing the C-NPs (negatively charged due to C-oligo) is pipetted to the assay unit, a single C-NP is electrostatically guided and placed onto a center position of each circular pattern via electrostatic funneling and self-limiting single-particle placement mechanism; here the positively and negatively charged SAMs electrostatically guide C-NPs toward the centers of the circular holes. The APTES SAMs on the Cr surface are subsequently removed by immersing the assay unit into an aqueous solution at 42° C. for two and half hours, which leaves the Cr surface negatively charged in the pH range of the experiment (pH: 7.7 for the hybridization), preventing the adsorption of the negatively charged T-oligo's and P-NPs in the subsequent processes. (g) Introduction of the T-oligo solution and then P-NP solution produce nanoparticle-bridge conjugates, where the P-NP provides a bridge between the Au layer (drain electrode) and the C-NP in contact with the Cr layer (source electrode). (h) The formation of nanoparticle-bridge conjugates is electrically detected by applying a voltage bias across the drain (Au) and source (Cr) electrodes, and measuring the current. (i) A three-dimensional view of panel (h) is shown in panel (i).

Example 4

Quantitation of Nucleic Acids and Polypeptides

Figure 5:
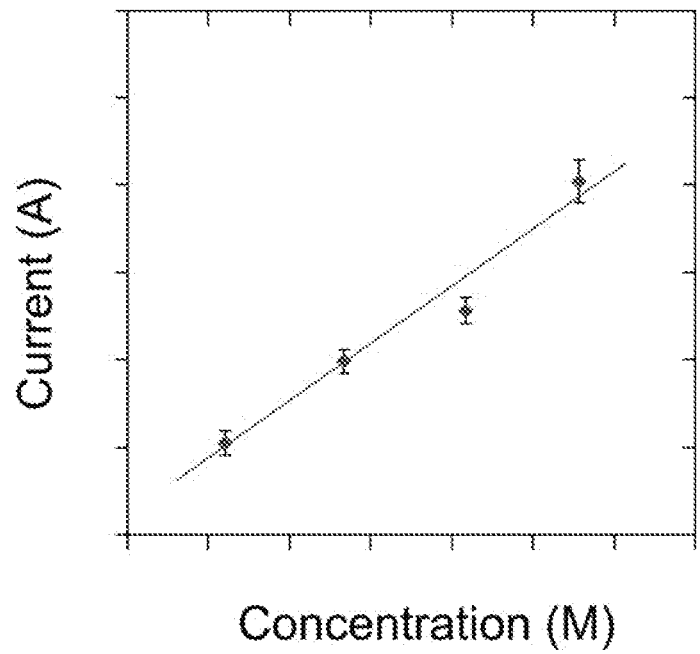
FIG. 5 shows a schematic of the correlation between the current (Amps) and the concentration of the oligonucleotide target (M). The resulting graph shows the linear quantitation of the target molecules over a range of concentrations.

The single-particle bridge assay (SPBA) provides for improved detection of very low levels of molecules, including nucleic acids and polypeptides. Because the formation of a current in the SPBA assay can occur even with the binding of one probe nanoparticle, the SPBA assay also provides for improved quantitation at very low levels of oligonucleotide (or antigen) concentration. As shown in the example of FIG. 5, there is a linear relationship when measuring the current (Amps) over a range of concentrations for the oligonucleotide target (M). Thus, the SPBA assay can be used to quantify the amount of oligonucleotides (or antigen) present in a particular sample when necessary.

Example 5

Single-Particle Bridge Assay for Detection of Non-Biological Molecules

Figure 6A:
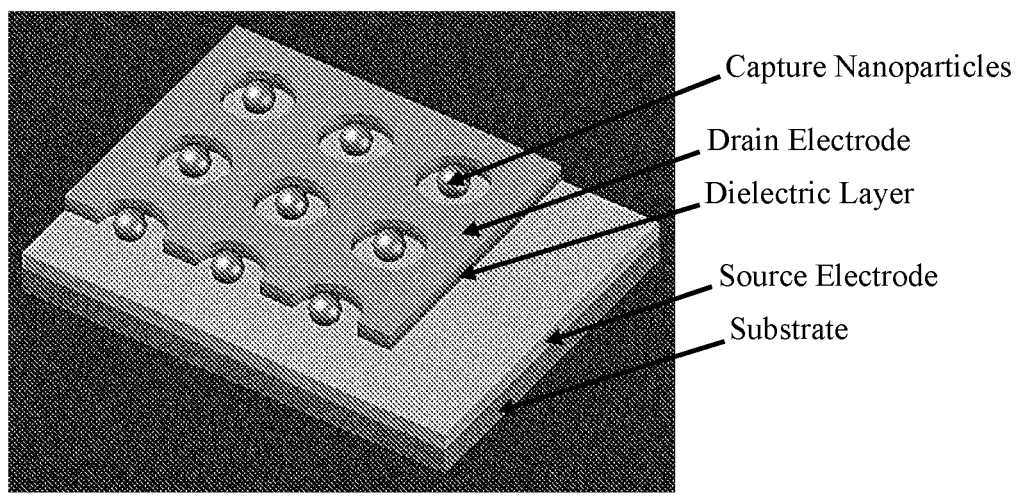
FIG. 6A shows a schematic of the single-particle bridge assay (SPBA) device set up prior to the detection of a non-biological molecule. The capture nanoparticles (C-NPs) are electrostatically funneled into the center locations of the circular holes of the drain electrode and dielectric layer. The drain electrode is electrically separated from the source electrode by a dielectric layer. The capture nanoparticle is in contact with the source electrode.
Figure 6B:
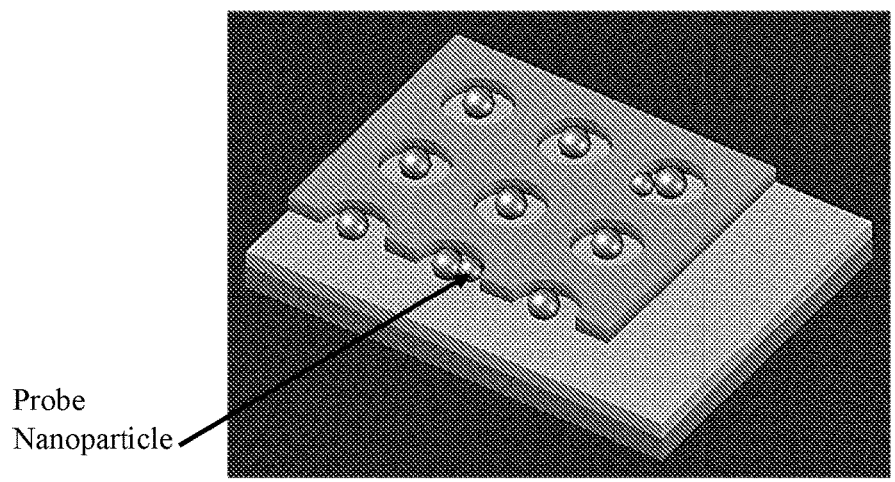
FIG. 6B shows the single-particle bridge assay schematic after addition of the target molecule (T-molecule) and the probe nanoparticle (P-NP). The capture nanoparticle (C-NP) is a nanoparticle on which capture molecules (C-molecule) are attached. Nanoparticle-bridge conjugates are formed that electrically bridge the drain electrode and source electrode (capture, target, and probe molecules are not shown in FIGS. 6A and 6B for image clarity).
Figure 6C:
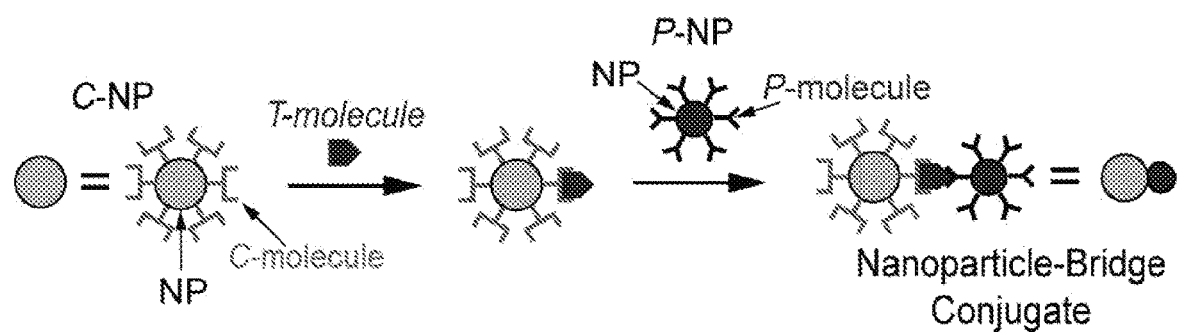
FIG. 6C shows a schematic of the formation of the single nanoparticle bridge conjugate. The probe nanoparticle (P-NP) is a nanoparticle on which probe molecules (P-molecule) are attached. The capture molecule (C-molecule) binds to one portion of the target molecule (T-molecule) and the probe molecule (P-molecule) binds to a remaining portion of the T-molecule. Formation of the single-particle bridge can be electrically detected.

The use of the single-particle bridge assay (SPBA) for the detection of non-biological molecules (for example, an explosive such as TNT) is illustrated in FIGS. 6A-6C. First, capture nanoparticles (C-NPs) on which capture molecules (C-molecule) are immobilized are placed at the center positions of the circular holes of the drain electrode and the circular holes of the dielectric layer (FIG. 6A). Here, the assay unit is fabricated on a substrate (e.g., Si wafer) with three different material layers (source electrode (e.g., Cr), dielectric layer (e.g., $SiO_2$), and drain electrode (e.g., Au)) arranged in a configuration in FIG. 6A, in which the insulating layer (dielectric layer; e.g., $SiO_2$) electrically disconnects the top drain electrode (e.g., Au layer) from the source electrode (e.g., metal Cr layer). The capture nanoparticles (C-NPs) are in contact with the source electrode.

In the next step, a solution containing target molecules (T-molecule) and probe nanoparticles (P-NPs: nanoparticles with a probe molecule (P-molecule) attached) is introduced and the presence of the T-molecules leads to the formation of nanoparticle-bridge conjugates, which electrically bridge the drain electrode (e.g., Au layer) and the source electrode (e.g., metal Cr layer) (See FIG. 6B).

The formation of the nanoparticle-bridge conjugates is further illustrated in FIG. 6C. Briefly, a T-molecule is captured by a C-NP through binding between the T-molecule and the capture molecules (C-molecule). When probe nanoparticles (P-NPs; abundant) on which probe molecules (P-molecule) are immobilized are introduced, a P-NP is captured by the C-AuNP through binding between the P-molecule and the T-molecule, producing a nanoparticle-bridge conjugate (FIG. 6C). The final nanoparticle-bridge conjugate of the single-particle bridge assay (SPBA) (See FIGS. 6B and 6C) is electrically detected by applying a voltage bias between the source electrode (e.g., Cr layer) and the drain electrode (e.g., Au layer) and measuring the current.

Example 6

Single-Particle Bridge Assay (SPBA) Portable Kit

Figure 12A:
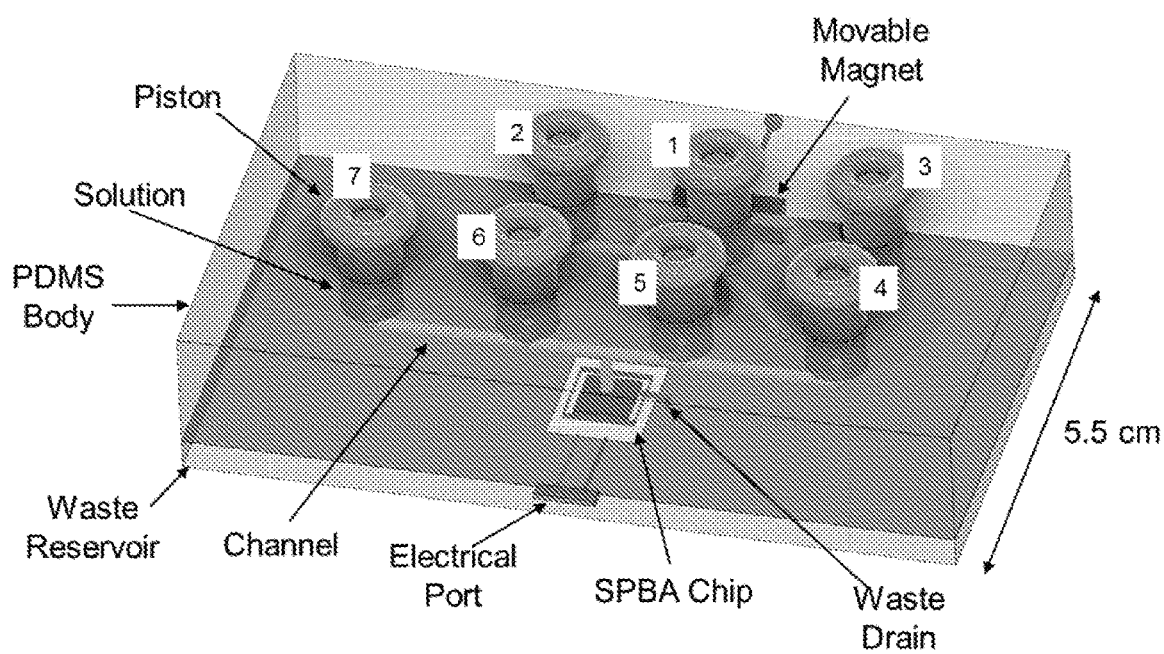
FIG. 12A shows a prototype design for a portable SPBA kit. The piston/solution units (#1-#7) contain the following. 1: M-oligo/MMP solution (used to eliminate background DNA/RNA; M-oligo: oligo which is complementary to the target oligo; MMP: magnetic micro-particle), 2: washing buffer, 3: deionized water, 4: hybridization buffer, 5: stringency washing buffer, 6: P-NP solution, 7: washing buffer. Pushing down a piston by a finger breaks the membrane at the bottom of a solution container and releases the solution to the channel. The DNA/RNA sample is introduced into the piston/solution unit #1. The background DNA/RNA is removed in unit #1-#3 in the following procedure: 1) the target DNA/RNA is captured by M-oligo/MMP in unit #1, 2) the movable magnet is applied to collect the MMP's to the container wall, 3) by pushing down the piston in #2 unit, the washing buffer is released and enters into #1 unit, which removes the background DNA/RNA, 3) by pushing down the piston in unit #3, deionized water is released and enters into #1 unit, 4) the magnet is removed from the wall, 5) the target DNA/RNA is released from the M-oligo/MMP's due to the DI water, 6) by applying the magnet again, all MMP's are collected at the container wall, 7) the target DNA/RNA solution is transferred to unit #4 by pushing down the piston in #1. When no magnetic elimination of background DNA/RNA is needed, the target solutions can be directed introduced to #4 unit.
Figure 12B:
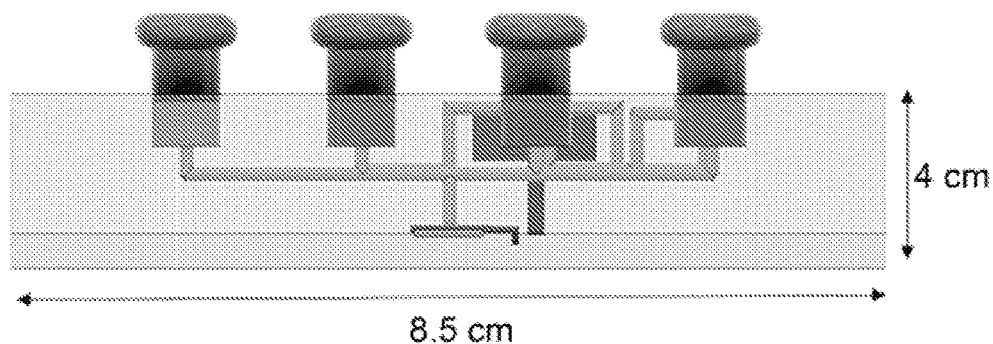
FIG. 12B shows a cross-sectional view of the side of the prototype design for a portable SPBA kit.

The SPBA portable kit is comprised of a small SPBA chip and an auxiliary system that delivers solution (buffers and target solutions) into the SPBA chip (FIG. 12). The dimension of a single SPBA chip is about 5 mm×7 mm or smaller. A single SPBA chip can contain many subunits and each subunit can be used for detection of different (or the same) sequences of DNA and/or RNA. A multi-disease detection (e.g., simultaneous detection of Zika, Ebola, Dengue, HIV, Anthrax, Smallpox, etc.) on a single SPBA chip is performed by having each subunit to contain C-NP's that selectively capture specific target DNA/RNA molecules of interest. Each subunit also may detect different sections of DNA/RNA of the same disease (for example, sequence number 1020-1055, 2256-2290, 7226-7257, and 9910-9944 of Zika virus RNA), which reduces false positive and false negative to near zero.

The SPBA portable kit has a dimension of about a credit card size and is designed to be operated manually. Further miniaturization and fully automated operation can be done using microfluidics. The SPBA portable kit is composed of a PDMS (polydimethylsiloxane) body, channels for solution flow, a waste reservoir, pistons (plastics), a magnet, and electrical connections (FIG. 12). The PDMS body with channels and waste reservoir can be built using the well-established PDMS procedure, involving pouring PDMS to the molds, curing, and removing molds, where molds are used for formation of the channels and the spaces to accommodate the pistons/solutions. The piston/solution unit is made of a piston, solution (such as buffers, MMP solution, and P-NP solution), and solution container having a membrane at the bottom. When the piston is pushed down with a finger, the membrane breaks and releases the solution to the channel.

The SPBA portable kit operates as follows. The sample is a small volume (typically, 100 μL-1 mL) of solution containing target DNA/RNA. The SPBA chip has C-NPs that have already been placed between electrodes. The kit operation only needs sequentially pushing down the pistons and applying the magnet. The sample solution is introduced to #1 piston/solution unit (M-oligo/MMP solution: to eliminate background DNA/RNA; M-oligo: oligo which is complementary to the target oligo; MMP: magnetic micro-particle) and the background DNA/RNA is eliminated by applying #2 and #3 units along with use of the magnet (detail in the figure caption). The target solution (background DNA/RNA eliminated) is sent to #4 unit. By pushing down the piston of #4 unit, the target solution is sent to the SPBA chip, where target DNA/RNA is captured. Pushing down the piston of the #5, #6, and #7 units, sends the stringency buffer, P-NP solution, and final washing buffer to the SPBA chip, respectively (with appropriate time intervals between steps). The electrical assay output is obtained by connecting a current (or resistance) measurement cartridge (e.g., a commercially available portable multi-meter with Bluetooth connection) to the electrical port of the SPBA prototype. The electrical readout is sent to a smartphone, tablet, or laptop through Bluetooth connection. The SPBA portable kit in FIG. 12 is a disposable kit. The total cost to produce one SPBA prototype is small. With scaled-up mass production, the unit price can go down even further.

Example 7

Various Configurations of C-NPs

Figure 13A:
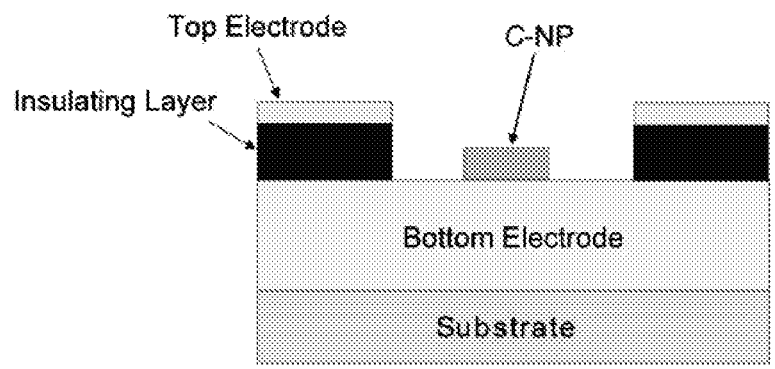
FIG. 13A show a schematic for the preparation of the single-particle bridge assay device where the capture nanoparticles (C-NPs) can be positioned on top of the bottom electrode.
Figure 13B:
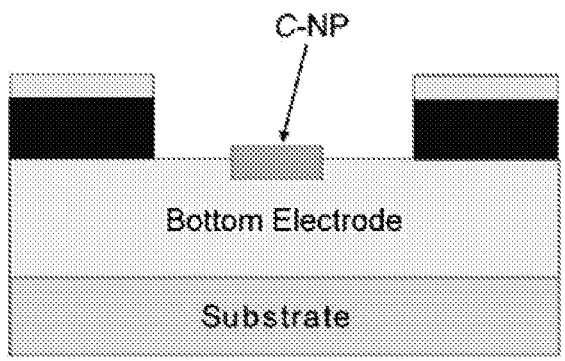
FIG. 13B show a schematic for the preparation of the single-particle bridge assay device where the capture nanoparticles (C-NPs) can be positioned partially embedded in the bottom electrode.
Figure 13C:
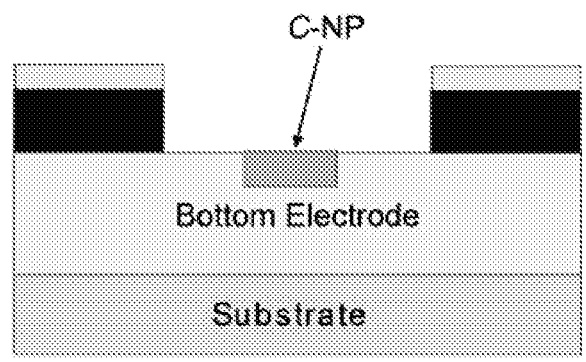
FIG. 13C show a schematic for the preparation of the single-particle bridge assay device where the capture nanoparticles (C-NPs) can be positioned fully embedded in the bottom electrode.

The capture nanoparticles (C-NPs) can take various geometrical configurations such as sphere, wire, and disk. C-NPs can also be positioned in a variety of configurations. FIG. 13 shows examples for the variations of C-NP positioning: (a) On top of the bottom electrode; (b) Partially embedded in the bottom electrode; or (c) Fully embedded in the bottom electrode. The embedded C-NP configurations (FIG. 13b-13c) can be made using known CMOS fabrication technologies (involving lithography, etching, and deposition, etc.).

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

I claim:

1. A device, comprising:
an electrically-insulating substrate; and
a first detecting unit, comprising:
a source electrode disposed on the electrically-insulating substrate;
a drain electrode; and
a dielectric layer;
wherein the dielectric layer is disposed between the source electrode and the drain electrode;
wherein the drain electrode and the dielectric layer comprise an array of holes;
wherein the holes in the drain electrode and the dielectric layer are aligned; and
at least one capture unit, comprising:
a capture nanoparticle;
wherein the capture nanoparticle is in contact with the source electrode; and wherein the nanoparticle is substantially centered in the holes of the drain electrode and the dielectric layer;
and wherein the capture nanoparticle is a metal, semiconductor, or magnetic nanoparticle.

2. The device of claim 1, further comprising:
a probe nanoparticle;
wherein the probe nanoparticle forms a nanoparticle-bridge conjugate with the capture nanoparticle in the presence of a target molecule;
wherein the probe nanoparticle in the nanoparticle-bridge conjugate provides an electrical path between the capture nanoparticle and the drain electrode.

3. The device of claim 1, further comprising:
a first oligonucleotide target;
wherein the capture nanoparticle comprises a first single-stranded oligonucleotide having a first nucleotide sequence complementary to a portion of the first oligonucleotide target; and
wherein the capture nanoparticle is a metal, semiconductor, or magnetic nanoparticle; and
a plurality of probe nanoparticles;
wherein the probe nanoparticles comprise at least one nanoparticle and a probe oligonucleotide complementary to at least a portion of the first oligonucleotide target different than the portion complementary to the first nucleotide sequence; and
wherein the probe nanoparticle is a metal, semiconductor, or magnetic nanoparticle.

4. The device of claim 1, wherein the device further comprises:
a polypeptide target;
wherein the capture nanoparticle comprises a first antibody having an affinity for the polypeptide target; and
wherein the capture nanoparticle is a metal, semiconductor, or magnetic nanoparticle; and
a plurality of probe nanoparticles;
wherein the probe nanoparticles comprise at least one nanoparticle and a second antibody capable of binding an unbound portion of the polypeptide target; and
wherein the probe nanoparticle is a metal, semiconductor, or magnetic nanoparticle.

5. The device of claim 1, further comprising:
a target molecule;
wherein the capture nanoparticle comprises a capture molecule having an affinity for the target molecule; and
wherein the capture nanoparticle is a metal, semiconductor, or magnetic nanoparticle; and
a plurality of probe nanoparticles;
wherein the probe nanoparticles comprise at least one nanoparticle and a probe molecule capable of binding an unbound portion of the target molecule; and
wherein the probe nanoparticle is a metal, semiconductor, or magnetic nanoparticle.

6. The device of claim 1, further comprising:
a plurality of second detecting units, each second detecting unit comprising:
an electrically-insulating substrate;
a source electrode disposed on the electrically-insulating substrate;
a drain electrode; and
a dielectric layer;
wherein the dielectric layer is disposed between the source electrode and the drain electrode;
wherein the drain electrode and the dielectric layer comprise an array of holes;
wherein the holes in the drain electrode and the dielectric layer are aligned; and
at least one capture unit, comprising:
a capture nanoparticle;
wherein the capture nanoparticle is in contact with the source electrode; and wherein the nanoparticle is substantially centered in the holes of the drain electrode and the dielectric layer.

7. The device of claim 1, wherein the source electrode is selected from the group consisting of Cr, Ti, Mo, W, Si, GaAs, and InP.

8. The device of claim 7, wherein the source electrode is chromium (Cr).

9. The device of claim 1, wherein the drain electrode is selected from the group consisting of gold, silver, titanium, and copper.

10. The device of claim 9, wherein the drain electrode is gold.

11. The device of claim 1, wherein the dielectric layer is selected from the group consisting of $SiO_2$, $Si_3N_4$, $HfO_2$, and $Al_2O_3$.

12. The device of claim 11, wherein the dielectric layer is $SiO_2$.

13. The device of claim 1, wherein the electrically-insulating substrate is silicon, silicon dioxide, or a combination thereof.

14. The device of claim 13, wherein the electrically-insulating substrate is silicon dioxide.

15. The device of claim 1, wherein the source electrode and drain electrode are comprised of different metals.

16. The device of claim 15, wherein the source electrode is chromium and the drain electrode is gold.

17. The device of claim 1, further comprising an electrical reading device for interrogating the device.

18. The device of claim 1, further comprising a portable electrical reading device for interrogating the device.

19. A method of detecting nucleic acid hybridization, comprising:
providing a device of claim 1;
providing a first oligonucleotide target;
wherein the capture nanoparticle comprises a first single-stranded oligonucleotide having a first nucleotide sequence complementary to a portion of a first oligonucleotide target;
wherein the first oligonucleotide target hybridizes a portion of the first nucleotide sequence thereby leaving an unhybridized portion of the first oligonucleotide target;
providing a plurality of first probe nanoparticles under hybridizing conditions;
wherein the first probe nanoparticles comprise at least one nanoparticle and a probe oligonucleotide complementary to the unhybridized portion of the first oligonucleotide target;
wherein the nanoparticle in the first probe nanoparticle is a metal, semiconductor, or magnetic nanoparticle;
applying a voltage drop across the electrodes; and
measuring a change in conductivity, resistivity, capacitance, or impedance across the electrodes at known locations to determine complementarity of the oligonucleotide target to the first nucleotide sequence and complementarity of the oligonucleotide target to the probe oligonucleotide sequence.

20. A method of detecting a polypeptide, comprising:
providing a device of claim 1;
wherein the capture nanoparticle is comprised of a plurality of first antibodies attached to the nanoparticle; and wherein the capture nanoparticle is a metal, semiconductor, or magnetic nanoparticle;
providing a polypeptide target;
wherein the first antibodies have an affinity to a portion of the polypeptide target;
providing a plurality of first probe nanoparticles under hybridizing conditions;
wherein the first probe nanoparticles comprise at least one nanoparticle and a second antibody capable of binding an unbound portion of the polypeptide target;
wherein the probe nanoparticle is a metal, semiconductor, or magnetic nanoparticle; applying a voltage drop across the electrodes; and measuring a change in conductivity, resistivity, capacitance, or impedance across the electrodes at known locations to determine binding of the polypeptide target to the first antibodies and to determine binding of the polypeptide target to the second antibodies.

21. A method of detecting a non-biological molecule, comprising:
providing a device of claim 1;
wherein the capture nanoparticle is comprised of a plurality of first molecules attached to the nanoparticle; and wherein the capture nanoparticle is a metal, semiconductor, or magnetic nanoparticle;
providing a target molecule;
wherein the first molecules have an affinity to a portion of the target molecule;
providing a plurality of first probe nanoparticles under hybridizing conditions;
wherein the first probe nanoparticles comprise at least one nanoparticle and a probe molecule capable of binding an unbound portion of the target molecule;
wherein the probe nanoparticle is a metal, semiconductor, or magnetic nanoparticle; applying a voltage drop across the electrodes; and
measuring a change in conductivity, resistivity, capacitance, or impedance across the electrodes at known locations to determine binding of the target molecule to the first molecule and to determine binding of the target molecule to the probe molecule.

\* \* \* \* \*

SEQUENCE LISTING

<160> NUMBER OF SEQ ID NOS: 6

<210> SEQ ID NO 1
<211> LENGTH: 38
<212> TYPE: DNA
<213> ORGANISM: Artificial Sequence
<220> FEATURE:
<223> OTHER INFORMATION: Synthetic Construct

<400> SEQUENCE: 1
tttttttttt tttttttttt atccttatca atatttaa                    38

```
<210> SEQ ID NO 2
<211> LENGTH: 30
<212> TYPE: DNA
<213> ORGANISM: Artificial Sequence
<220> FEATURE:
<223> OTHER INFORMATION: Synthetic Construct

<400> SEQUENCE: 2
taggaatagt tataaattgt tattagggag                              30

<210> SEQ ID NO 3
<211> LENGTH: 32
<212> TYPE: DNA
<213> ORGANISM: Artificial Sequence
<220> FEATURE:
<223> OTHER INFORMATION: Synthetic Construct

<400> SEQUENCE: 3
caataatccc tctttttttt tttttttttt tt                           32

<210> SEQ ID NO 4
<211> LENGTH: 38
<212> TYPE: DNA
<213> ORGANISM: Artificial Sequence
<220> FEATURE:
<223> OTHER INFORMATION: Synthetic Construct

<400> SEQUENCE: 4
tttttttttt tttttttttt gacgtccgtg tcgacgcg                     38

<210> SEQ ID NO 5
<211> LENGTH: 32
<212> TYPE: RNA
<213> ORGANISM: Artificial Sequence
<220> FEATURE:
<223> OTHER INFORMATION: Synthetic Construct

<400> SEQUENCE: 5
cugcaggcag cagcugcgcg ugcugcccag aa                           32

<210> SEQ ID NO 6
<211> LENGTH: 33
<212> TYPE: DNA
<213> ORGANISM: Artificial Sequence
<220> FEATURE:
<223> OTHER INFORMATION: Synthetic Construct

<400> SEQUENCE: 6
cacgacgggt cttttttttt tttttttttt ttt                          33
```